(12) United States Patent
Brown

(10) Patent No.: US 12,023,229 B2
(45) Date of Patent: *Jul. 2, 2024

(54) FORM-FITTING, ERGONOMIC MENSTRUAL DEVICE WITH EASY TO REACH REMOVAL STEM

(71) Applicant: Christine Beatrice Brown, Carpinteria, CA (US)

(72) Inventor: Christine Beatrice Brown, Carpinteria, CA (US)

(73) Assignee: Wevotopia LLC, Carpinteria, CA (US)

( * ) Notice: Subject to any disclaimer, the term of this patent is extended or adjusted under 35 U.S.C. 154(b) by 634 days.

This patent is subject to a terminal disclaimer.

(21) Appl. No.: 17/308,553

(22) Filed: May 5, 2021

(65) Prior Publication Data

US 2021/0251815 A1 Aug. 19, 2021

Related U.S. Application Data

(63) Continuation-in-part of application No. 16/237,172, filed on Dec. 31, 2018, now Pat. No. 11,096,819.

(51) Int. Cl.
*A61F 13/00* (2024.01)
*A61F 13/20* (2006.01)

(52) U.S. Cl.
CPC ........ *A61F 13/2045* (2013.01); *A61F 13/204* (2013.01); *A61F 13/208* (2013.01)

(58) Field of Classification Search
CPC ... A61F 13/2045; A61F 13/204; A61F 13/208
See application file for complete search history.

(56) References Cited

U.S. PATENT DOCUMENTS

2019/0388264 A1* 12/2019 Russe .................. A61H 19/32
2020/0214876 A1* 7/2020 Tsai ..................... A61F 5/4553

* cited by examiner

*Primary Examiner* — Steven O Douglas
(74) *Attorney, Agent, or Firm* — Lowry Blixseth APC; Scott M. Lowry

(57) ABSTRACT

An asymmetrical menstrual device is disclosed, with functional pressure points that aid in the insertion, opening, and removal of the device and requires minimal contact with the device itself, as well as with the body while placing inside the vaginal canal. Major design elements support ease of placement and effective opening of the device to create a seal, while minimizing pressure in sensitive areas. Another design feature is the length, functionality, and malleability of the removal stem that can be adapted to any length up until the base of the device. These elements enable greater cleanliness, comfort, and overall ease of use.

19 Claims, 22 Drawing Sheets

FORM-FITTING, ERGONOMIC MENSTRUAL DEVICE WITH EASY TO REACH REMOVAL STEM

CROSS-REFERENCE TO RELATED APPLICATION

This application is a continuation-in-part of U.S. application Ser. No. 16/237,172 filed on Dec. 31, 2018, entitled "Menstrual Device with Pressure Points and Elongated Removal Stem." The above-referenced application is incorporated herein by reference in its entirety.

FIELD

A menstrual device with pressure points, asymmetrical shape, elongated removal stem, and various elements that provide more comfort and ease during insertion, during wear and usage, and removal. A major part of the device is the method to apply pressure and fold the device with one hand, thereby allowing minimal contact to the device.

BACKGROUND

Menstrual cups (also sometimes referred to as "devices") are products that are placed within the vaginal canal and allow the user to collect menstrual fluid. The materials used can vary, but should include medical grade silicone for safety and hygienic purposes. Cups can be reused for several years, pending proper care, thereby reducing the overall cost and amount of waste that other menstrual products, such as pads and tampons, create. Cup options have been on the rise in the marketplace, but there has been a need for designs that address discomfort, sometimes even pain associated with insertion, removal, as well as the difficulty in creating a proper seal that diminishes the likelihood of leakage. Cups often require two hands to properly fold or pinch down the material and then put in place, and often require additional skin contact with the labia, as well as within the vaginal canal, to ensure it is properly placed with the seal of the upper ring intact. This can be problematic as placing or removing a cup can be messy and access to running water or other means to clean the cup prior to re-insertion and wash one's hands can sometimes be limited.

SUMMARY

By designing a menstrual device that is asymmetrical, this enables greater comfort and functionality during insertion and removal, and also reduces the possibility of leakage due to the unique integrity of the device shape that lends itself to fully opening once placed in the vaginal canal.

The disclosed design features provide a menstrual device in which comfort, functionality, and methods for insertion and removal are major elements of the overall asymmetrical shape.

The base of the device extends into an elongated stem that can be adapted by the user to their desired length; that is, to any length up until the base of the device. The elongated stem also minimizes the need for additional skin contact or possible probing inside the vaginal canal to establish the device location.

The base of the device exhibits areas with functional pressure points for collapsing the device with one hand instead of two; ensuring a full pop-open or seal of the upper ring when placed in the vaginal canal; and enabling a gentle breaking of the seal for comfort and ease of removal.

Further features, advantages and properties of the device associated with this application, will become clear in the detailed descriptions.

BRIEF DESCRIPTION OF THE DRAWINGS

In the following detailed section of the present description, the elements of the present application will be explained in greater detail with reference to the example embodiments included in the drawings, in which.

DETAILED DESCRIPTION

Figure 1:
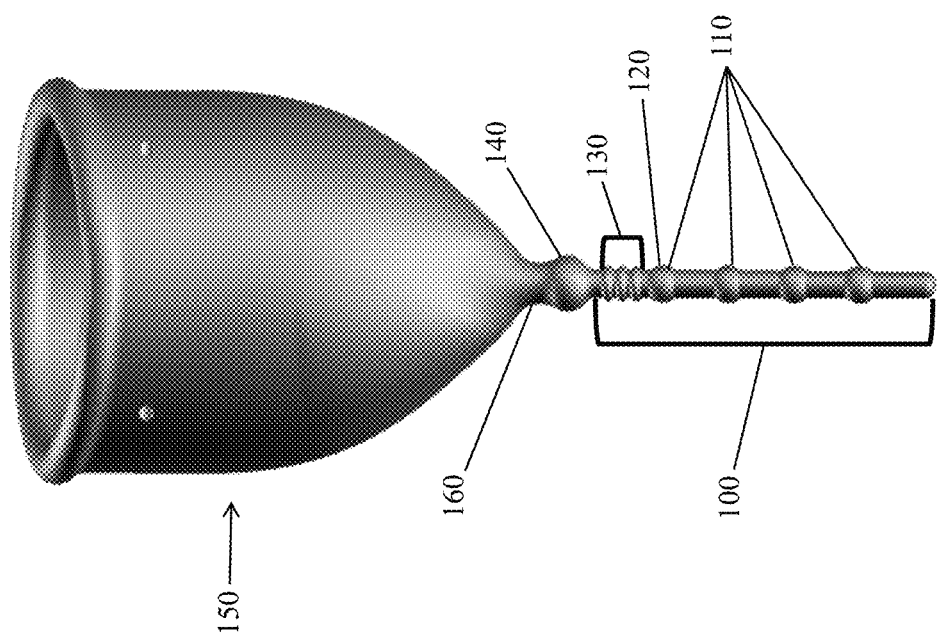
FIG. 1 is a perspective view of a menstrual device from the front with an elongated removal stem in accordance with aspects of the present invention.

The vaginal cavity is quite adaptable and varies slightly with each individual. The vaginal cavity is where menstrual blood exits from the cervix in various amounts for a duration, typically, of several days each month. Methods and products for menses range from absorption, with pads and tampons, to collection, with catamenial devices, now more commonly known as menstrual cups.

Menstrual cups provide a healthy and sustainable alternative to the waste accumulating one-time usage of pads and tampons. Menstrual cups can be made from silicone via a liquid silicone rubber, silicone injection molding process, and with proper care can be used for several years. However, it is challenging to find a product that has gone through the full certification and validation processes. This can impact the overall quality in available products, ranging from the materials used, to their manufacturing and post-manufacturing processes, resulting in products that may be suspect.

Menstrual cups, with increasing popularity and awareness, has become a more common menstrual solution, especially amongst those who wish to reduce waste and save money with a healthy alternative. However, many users are hindered by the needed body contact to place and remove the cup and fear it will be messy. To properly place a traditional menstrual cup, the user will need to pinch or press down the sides of the cup wall, to collapse it and make it smaller for insertion. This, traditionally, has required contact on all outer wall surfaces of the cup and the use of two hands. Similar to a tampon, the cup is then inserted into the vaginal canal, where it will need to open, or unfold, in order to ensure a seal. The goal of the seal, which is achieved by continuous contact on the sides of the vaginal wall by the upper ring of a cup, is to prevent the possibility of leakage. Most cups will require the user to have additional physical contact of their labia, as well as inside their vaginal walls, to check and make sure a cup is properly placed and fully open, thereby creating the desired seal for collection. This process sometimes involves: manual examination within the vaginal cavity with a finger along all sides of the wall to check for a folded area or crease; additional cup rotation within the vaginal canal with hopes that it will eventually open fully; or other similar actions, which is more involved than many might be comfortable with, and can be messy. There is not always access to clean, running water, so this part of the process might prove problematic for some, increasing the risk of being unhygienic in those instances. Further, checking to make sure a cup is properly placed each time might take more time than some prefer. However, cups generally have a larger capacity than tampons or pads, so some users are able to go up to twelve hours between emptying their cup. Thus, such users can plan accordingly and wait until they are in a more favorable location to wash their hands and empty the cup, also saving time overall due to less frequent changing demands compared to tampons or pads.

Some cups try to avoid this additional contact inside the vaginal canal to check or manually create a seal, by designing a thick or stiff upper ring that has a stronger pop-open, but this, in turn, might be painful or uncomfortable for some users. Further, having increased pressure at the top of the cup, that is the furthest distance into the vaginal cavity, can create an undesired effect of additional pressure on the urethra and colon, creating a sensation of needing to urinate, or restricting that process. It can also create a sensation of blockage or constipation in the user when it comes to bowel movements. The female anatomy of the urethra and colon are closer in proximity to the vaginal cavity the further into the vaginal canal one goes. Conversely, there is less impact on other bodily functions or discomfort if there is rigidity or pressure closer to the vaginal opening where the spacing of the urethra and colon are further from the vaginal canal. Furthermore, when it is time to remove and empty the cup, the thick or stiff upper ring that is no longer collapsed like it was during insertion, but fully open, can cause pain for some users in that it is a much larger area that is being removed from the vaginal canal.

Most cups, while they are malleable, are symmetrical in shape, which does not take into account the overall shape of the vaginal cavity. This can create slight discomfort and awareness when a symmetrical cup is being used. Sometimes those cups go beyond discomfort and cause irritation, rubbing or rashes, soreness, bruising of the cervix, near the public bone, or other areas in or near the vaginal canal, in part, due to their symmetrical shape. It should also be noted that small holes can be seen near the upper ring of most cups, which help to maintain a balance in bodily fluids and relate to the effectiveness of the seal.

Removal of the cup to empty, clean, and reinsert if still menstruating, can require intimate contact as opposed to a pad or tampon, which can be removed with an attached string. Most cups have a base with little or no material to grasp and pull the cup down and out of the vaginal cavity. Some have a base or stem that extends to almost an inch in length and are not necessary for the overall function of the cup and can be cut or removed completely if the user desires due to having a lower cervix, or if they have sensitivity to the often abrasive material extending out from the stem to create a grip. The abrasive materials can cause friction, create discomfort, and sometimes even a rash, especially when extending from a cup base or stem that is quite substantial in material width. The stem in some cups may be covered with small "spikes" or the like, insofar that it might feel to a user like a stiff popsicle stick or straw with extending ladder rungs, or like rough sandpaper against delicate tissues. In cups with minimal or no stem at the base, the user might need to search for the cup by reaching up and into the vaginal cavity because the cup might have shifted higher or out of place during use, especially in the case of individuals who have a higher cervix. This can prove problematic, again, in cases where one cannot properly clean their hands before or after, or in situations where someone might have longer fingernails, as they might inadvertently scratch themselves, or damage the cup as they try to grab hold of the cup and pull it out for removal.

Once the user has hold of the cup, due to the often stiff upper ring that is now fully open, resulting in a much larger surface area and circumference than the previously collapsed cup for insertion, removal can sometimes create discomfort or even pain for the user. This, along with some of the many other aspects found in traditional cups described above, can deter someone from continuing usage of a cup.

Therefore, it is the aim of this present design to address prevalent limitations and provide a more comfortable, functional, and reliable menstrual device. Such a design, while being more user friendly for first-time and long-time cup users, may also benefit individuals with disabilities, due to a more functional and user-friendly insertion and removal process. Additionally, considering social and cultural stigmas and taboos often still surrounding menstruation, female bodies, and physical contact, this particular design may help alleviate stigmas insofar as the device requires far less physical contact for placement and removal compared to traditional cups. Further, it is of utmost importance that the material sourced and used for manufacturing has gone through extensive biological testing, in order to obtain regulatory clearance for medical device usage. Manufacturing aims to meet all federal requirements and is certified, registered, and listed to produce such medical devices, which is in opposition to current market trends where products do not always follow such procedures.

The material of the menstrual device may be made from medical grade silicone. The medical grade silicone may be designed to meet Current Good Manufacturing Practice, (cGMP) standards in facilities directly or indirectly regulated by US FDA (Food and Drug Administration). The liquid silicone rubber, or LSR, is designed for liquid injection molding, or LIM, as well as overmolding, which is another production option. The present design may also minimize production waste during the LIM process since the removal stem may also function as the channel in which the LSR travels within the tool or mold when manufacturing the menstrual device. In some devices, the material range can be 40 to 70 durometers, depending on specific design, function, and desired product feel. It should be noted that the device can be made with or without a removal stem, with or without additional grips on the stem or base or the cup, from alternate materials, with alternate manufacturing processes.

Alternatively, the material range may extend in softness by using 30 or even 20 durometers, depending on desired product outcomes and overall design dimensions. This present invention utilizes numerous embodiments unique to this design from prior inventions of similar menstrual devices.

Beginning at the uppermost sections, the device has material that protrudes outward as well as extends internally from the device walls. This feature enables a balance of comfort and function for users in that it minimizes pressure, particularly with respect to the bladder and urethra, as well as the colon, while fully open and placed within the vaginal canal. This differs from traditional devices, which often have thick, protruding upper rings that are often the most substantial portion of the device as they are dependent on that to create an effective seal. With this feature of an upper ring that is not overly thick, but in fact, has flexibility, it better enables an effective seal to form, which, in turn, moves with the user and minimizes and prevents the potential for leakage. With this present invention, the upper ring is not reliant on a thick or stiff upper ring, but in fact can feel more flexible in comparison to the device body or walls that instead, support the upper ring, in part, to fully open. Further, by not extending or protruding in excess outward from the device walls, pressure is reduced both after placement and during use, as well as during removal, which is unique from existing devices.

The upper ring, by also extending internally from the device walls, provides the necessary integrity to further support the upper ring fully opening to create an effective seal. Due to the unique flexibility still allowed, the upper ring is more readily adaptable to conform to the body of the user, who might have varying angles of their vaginal canal, differing shape throughout their cycle due to bowel movements and such, as well as varying cervix placement as that shifts naturally throughout the menstrual cycle as well.

The upper ring of this device is asymmetrical in that the front facing section begins to angle and slope towards the slightly shorter front wall of the device. This is unique from traditional, cone-shaped cups that do not slope, which creates unnecessary pressure for some cup users during use and can create discomfort and even pain during removal since the opened cup is of larger size when removing. This unique slope minimizes the pressure and device surface area while also assisting the user in safely breaking the seal during removal because of the angle of the upper ring that enables that during the side-to-side motion while pulling down gently, and again when the device reaches the vaginal opening. This feature thus also minimizes the potential of suctioning to the cervix, limits strain, discomfort, and even pain as it is gentler on the body in comparison to traditional devices.

This upper ring of asymmetrical design in this device further allows the cup to collapse in a more compact manner due to the reduction of material folding upon itself, since the difference in wall heights enables the upper ring to be slightly offset, thereby creating a smaller circumference when collapsed, which is unique to this design and enables a notably smaller point of entry for cup insertion. This is important for those especially with sensitivities or smaller vaginal morphology.

The front center of the upper ring also has the option to incorporate a slight dip, which serves to assist the hinge or area of collapse when creating the fold for insertion, as well as during removal, either naturally from the pressure exerted from the vaginal walls, or from applying pressure manually during removal. The upper ring can shift slightly from the upper wall both in the front and in the back sections so as to further reduce any additional pressure on the urethra or colon due to the unique ergonomic or asymmetrical nature of this design that enables such options for further comfort and function.

The body of this unique device is specifically shaped and curved to compliment the anatomical or ergonomic nature of the vaginal canal in relation to other organs and features such as the pubic bone. Unlike traditional cone shaped cups, or even ball shaped cups, this unique curve shaped cup is form fitting from the back wall curvature that lends itself well to different body positions such as standing or sitting, and the front wall mid height through the tapered section towards the base curves to accommodate the pubic bone. These unique design elements enable greater comfort, ease of placement in that, despite user experience, the cup will settle into the appropriate and effective placement, and further enables greater overall capacity for collection of menstrual fluids while not having expand out to a larger or more bulky feeling cup that could cause additional undesired pressure. The unique curvature further assists in the cup holding in place without the reliance on a substantial upper ring or overly intense suction seal since the combination of tapering towards the base as well as alignment with the pubic bone helps secure the cup. This is also particularly helpful for individuals who might have a weaker pelvic floor in that it compliments and better fits the overall vaginal anatomy and morphology, thus not relying on the upper ring intensity to create a seal and hold in place.

Unique to the cup body, due to the overall asymmetrical shape, the cup reinforces the overall integrity and is inclined to fully open after the collapsed cup is inserted for placement. This feature is particularly helpful as it means the cup opening is not solely reliant on the upper ring, but rather, is encouraged and supported by the unique shape of the cup body. This can further be supported by the internal spine which is unique in several capacities including reinforcement during collapsing the cup, as well as helping to support the cup opening again.

The front wall of this ergonomic cup body, with the shorter dimensions, has a pressure point in the area of the lower curve where the index finger would naturally settle to apply pressure for collapsing or folding the cup prior to insertion. This unique feature, in combination with the option of the internal spine, angle of the front upper ring, shift of the front upper ring diameter slightly towards the inner wall of the cup, and the dip or pitcher spout of the front upper ring that further supports the hinge and crease of the cup folding, in part, or in combination, enable this cup to be collapsed with one hand. This feature is of particular importance when it comes to individuals who might have limited mobility, for cleanliness in situations of limited water or means to clean the cup, and overall ease of use and improved experience with not having to touch the cup with both hands in numerous locations to achieve a similar result of collapsing the cup for insertion.

The side edges of the base of the cup, if needed, can have pressure exerted and due to the unique asymmetrical shape, further aids the cup fully opening from the base, as opposed to much higher up or having to manually create the space for the cup to fully open.

Last, the curvature of the cup walls supports greater comfort and ease during removal in that the now fully opened cup, with the shorter front wall, is able to safely break the seal with less reliance on user technique, which leads to a safer and less painful or messy removal. The pressure point used for collapse prior to insertion can also be utilized to help break the seal safely during removal.

The removal bulb is also unique in that it is asymmetrical. The front facing side is less bulbous or pronounced so as to minimize potential pressure if the cup placement shifts towards the pubic bone. The edges of the removal stem are wider, thus enabling a more effective grip, while still allowing great flexibility due to minimizing the overall dimensions due to being asymmetrical. Just above the removal bulb, the spacing is ergonomically aligned both with the pubic bone, as well as the needed space for most to comfortably grasp with their fingers a hold of the cup base. By being asymmetrical, one can easily identify whether the cup has fully opened to create a seal since the fold or crease in the cup can be identified from feeling if the base is fully flush. Further, it allows identifying the cup direction during placement from the base itself, which can be particularly helpful if changing at night or with little to no light for sighted individuals, while an identifiable reference for those who are blind.

The removal stem is pronounced in the length. This unique, elongated removal stem is notably useful for first time cup users who might not know how high their cervix is, and thus can at least have a much greater chance of locating and removing their cup with ease. It is also helpful for in the morning, after cups tend to migrate higher during sleep, or for those who have a higher cervix in general. This provides ease of mind, minimizes the need to probe, which can sometimes lead to anxiety, infection in the case of those with longer nails who might accidentally scratch themselves, or in some cases, the need for assistance from another person or a doctor to remove the cup.

Despite the elongated removal stem length, it is of specific dimensions to enable great flexibility for during use so that it is essentially unnoticeable to the user. The grip bulbs on the removal stem are also of varying dimensions to facilitate the balance between grip and comfort or flexibility. Culminating at or near the end of the removal stem is a larger removal bulb that enables an easier place to grasp which is helpful if the stem is slippery due to normal bodily discharge, additional menstrual fluids, or generally wet fingers. This, in combination with the elongated stem length, can assist in providing an overall better grip and less slippery fluids as it might extend and sit closer to the vaginal opening, thus readily positioned and easy to reach. Should a user not need the additional length due to preference, or lower cervix height, for example, then the removal grip bulbs can serve as an identifier of how much the user wants to cut once outside their body, and enables a more comfortable transition point, avoiding sharp edges remaining from being cut straight across with scissors, for the new hand-cut stem length.

The overall angle of the removal stem is shifted forward of the cup center positional line, which due to the ergonomic shape, also lends itself to ideal positioning for removal as the vast majority of users reach their cup for removal from the front of their body. This stem positioning also lends to greater overall comfort since the ergonomic curves compliment the body during a sitting position, which is in opposition to traditional cups that tend to poke directly down and cause discomfort and irritation. Lastly, though not suggested due to insurance, the unique curvature does also better facilitate penetration of various sorts during usage since the curves do not interfere as much as traditional cone shaped cups that can cause a poking sensation to a penis or fingers for example.

Alternatively, beyond the asymmetrical cup base, the removal bulb itself might be asymmetrical as well so as to minimize potential pressure against sensitive points of contact inside the vaginal canal or against the labia or vulva, depending on cup placement and how it sits. Additionally, this enables the user to identify the front of the cup by feel while allowing for a more extensive grip on the protruding sides of the bulb, that again, do not extend fully forward or back, minimizing potential discomfort and maintaining overall flexibility of the cup removal bulb at the base. The present design demonstrates the overall removal stem and cup base to be at an angle forward of the cup center line, thereby providing more comfort while sitting and avoiding the poking of cone-shaped cups that place their stem in center of base. This further allows for ease of locating the removal stem as well since it is already shifted slightly forward in the direction that the vast majority of cup users reach to grasp their cup when removing.

Additionally, the removal stem itself can be of varying width and grips as demonstrated here. Such variance provides flexibility, comfort, yet enough integrity and substance without the need to be overly thick, stiff, or irritating. The stem length itself is a feature for easy retrieval of the cup—especially in the case of new menstrual cup users who might not have any idea how high their cervix is, nor that the cervix can fluctuate in height throughout their menstrual cycle, thereby impacting how high up the vaginal canal the cup might shift and settle after initial placement. This feature is especially critical in that it can minimize the frustration, possible stress or trauma of being afraid the cup is stuck or out of reach, and in some more extreme cases, avoid having to have outside help from a friend, partner, doctor, or trip to the ER to retrieve the cup, thus also reducing the risk of potential infection from needless probing or prolonged time of insertion.

Additionally, this elongated removal stem helps secure the cup in place, thereby minimizing the cup shifting, rotating, and potentially causing spilling having migrated from initial placement.

Alternatively, the bulb at the base or end of the removal stem might enable additional future add-on features should a user have a much higher cervix and need an extension device. One such embodiment might be a connector that through rotation with a thread similar to that of a screw, might enable locking in, or some other similar feature.

Additionally, the overall embodiment as included here is of a form-fitting, ergonomic cup body that compliments the curvature found within the body and vaginal canal—the vaginal morphology. As mentioned previously, unlike traditional, cone or bullet shaped cups, this particular design is ergonomic so as to ensure greatest fit, effectiveness, and comfort for as many users as possible. The curvature of the cup body, the upper ring dimensions, cup base, removal bulbs, and removal stem orientation all take into account the natural body positioning while standing, sitting, with movement, so as to maximize optimal fitting and comfort in relation to relevant anatomy as previously mentioned.

The wider cup base, yet narrower front to back width allows comfort for those with smaller frames and bodies while still allowing increased capacity without having to enlarge or increase the overall geometric cup size or dimensions. This device also better accommodates varying body positions such as sitting and standing positions that shift our pelvis, thus impacting overall comfort and effectiveness of a cup. Further, the curvature of the front base of the cup compliments the placement in relation to the pubic bone and functions to assist overall cup placement while minimizing potential shifting or twisting of the cup. This curvature, in addition to helping secure the cup, is especially helpful for those with weakened pelvic muscles due to vaginal childbirth, or aging, for example, and helps hold the cup in place. Additionally, the more ergonomic shape allows users with a tilted uterus, or other such variations, more options to adjust the cup placement as best suits their bodies and needs, although by ergonomic design, this option simply proves more effective for such users compared to traditional cone-shaped cup options. Thus, the ergonomic shape and design provides an option for a greater range of users regardless of factors such as age, cervix height, tilted uterus, full term pregnancy or not. Overall, the ergonomic cup body creates less pressure on other organs and bodily functions, leads to comfort during use, during insertion due to a smaller circumference during collapse, and during removal as the angle of the upper ring and minimized protruding material allows the breaking of the seal by default, and at an earlier stage, whether the user knows to angle the cup or not. This minimizes potential stress and suction that might possibly be associated with prolapse with other cup designs that do not account for this. Additionally, less force is needed when collapsing the cup for insertion due to the asymmetry, internal spine, and upper ring, which allows this cup design to be successfully used with one hand if desired or needed.

Additionally, the form-fitting, asymmetrical cup creates an overall integrity of the cup fully opening to inhabit its full shape with ease, avoiding a more forceful pop open that often comes as a result of a thicker upper ring. This embodiment results in an upper ring that may be less firm than the cup body, thereby providing ease, comfort, and less pressure during removal when the upper ring is fully opened and a much larger width than the collapsed cup arrangement during insertion. Due to the integrity of the asymmetrical cup body, this cup upper ring can be less firm. An alternative embodiment is also disclosed, where turning the cup body inside out can provide the opposite effect, whereas the cup body becomes softer, while the upper ring becomes firmer if that option is preferred. In so doing, this embodiment exhibits the option of the inner diameter of the upper ring, that is flush with the cup walls, to minimize the overall outward extension and protrusion from the sides of the cup against the vaginal walls.

Additionally, due to the angled base of the form-fitting cup, though not a main focus, the design is more conducive to vaginal penetration and play compared to traditional conical cups, or even bulbous cups that often can interfere, create discomfort, and sit differently when placed in the vaginal canal.

It is noted that this list is not exhaustive as there may be other advantages not explicitly detailed herein. Further, the present application includes features and descriptions that can be implemented in combinations other than those explicitly described.

A first perspective of the menstrual device is illustrated in FIG. 1. The device 150 has a noticeably long and slender removal stem 100. Removal of the device 150 with the stem 100 should enable less probing if a user has a high cervix, or the device moves further up in the vaginal canal during wear, thus creating a safer and cleaner removal process. The existence of a removal stem is not unique per se, but this particular removal stem 100 is useful because it is noticeably elongated, yet remains highly flexible for increased comfort due to the stem width that does not need to be uniform in width, and can range from 1.5 mm to 6 mm. Removal stem 100 can be adapted to any length up until the removal bulb 140 or base of the device 160, by cutting the stem 100 to the desired length of the user. In some devices, the removal stem 100 may comprise small bulbs 120 that may vary in width and function both as a grip during removal or as a unique reference 110 for if a user wanted to shorten the stem. The user may do so by counting the number of bulbs 120 from the tip of the stem 100, removing the cup 150 from their body, then using that reference number to cut the stem 100, thereby eliminating what stem 100 length might not be needed for their body. The stem 100 can range in length from 0 mm, if removed, to just under 50 mm. Further comprising, the stem 100 is singly molded with the base of the device in uniform material, which due to the unique length and dimensions, is useful because it creates a reusable removal stem. Alternatively, users might otherwise have to add a one-time-use string, other material, or approach that might prove less healthy or sustainable in order to create additional length for ease of access.

In a second perspective view in FIG. 1, the stem 100 may further comprise of one or more removal grip rings 130 in the removal stem 100, providing traction while also minimizing potential for friction or discomfort from rough or protruding edges. The existence of additional material or grips 130 is not unique per se, but this particular placement of the grips 130 and unique contoured shape of the grips 130 and bulbs 120 assists in removal, while limiting potential for irritation. Alternatively, the device 150 is manufactured without the existence of the grips 130, removal stem 100, and/or the removal bulb 140 at the base 160.

Figure 2:
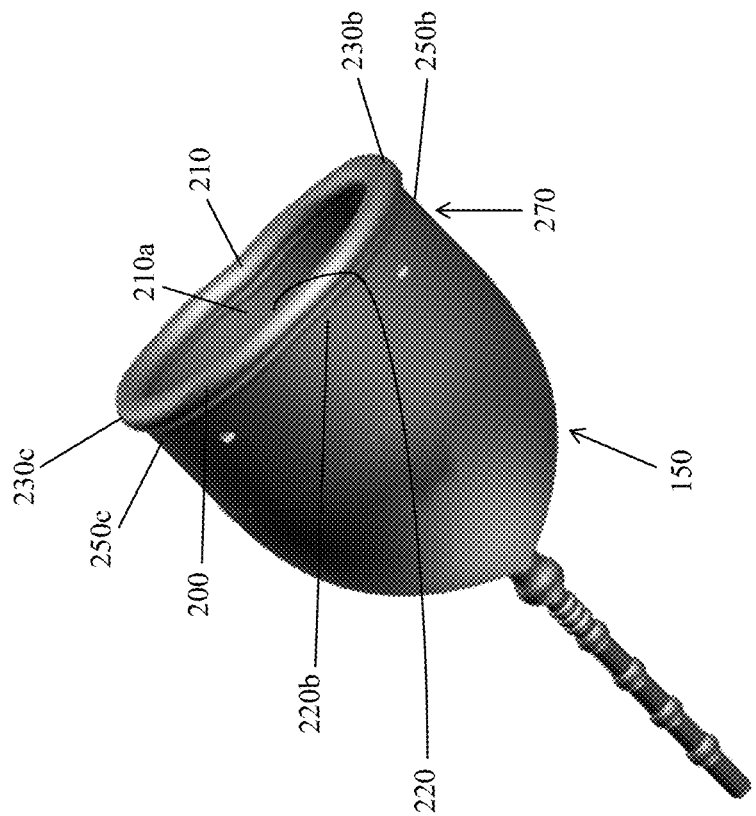
FIG. 2 is a perspective view from the back, with a slightly elevated angle, of the menstrual device of the present invention.

In the exemplary perspective view of FIG. 2, an upper ring 200 is viewed from the back, and slightly above, the cup 150. The existence of the upper ring 200 is not unique per se, but it should be noted that the upper ring 200 is not uniformly within the inner diameter of a cup wall 270, nor is it uniformly extending out as an outer diameter ring from the cup wall 270. It should be noted that this particular upper ring 200 is useful because it provides needed continued contact against the vaginal wall while minimizing pressure on other bodily functions. The inner diameter of the upper ring 200 for the front 210 and back 220 surfaces of the device ring 200 extend further into the interior dimensions of the device walls 210*a*, 220*b*, by a range of 0.5 mm to 6 mm. The right 230*c* and left 230*b* sides of the upper ring 200 extend outwards from the walls 250*c*, 250*b*, anywhere from 0.5 mm to 6 mm. The existence of the upper ring 200 extending outwards from the cup walls 270 is not unique per se, but this particular extension of the ring 200 outwards from the device wall 270 is substantial enough to assist in creating a seal when placed within the vaginal cavity, while not extending out in width to the point of creating intense pressure or rigidity due to excessive material volume dimensions. Further comprising, the upper ring 200, does not uniformly extend inside 210*a*, 220*b*, from the walls 270, nor outwards 230*b*, 230*c*, from the walls 270 as other devices, but this particular ring 200 design is useful in that it reduces or eliminates undue pressure, bruising, soreness, or discomfort due to a malleable and minimal material dimension that eliminates what is typically a stiff upper ring. It should be noted that the upper ring 200 at the front facing side 210 may reduce pressure in areas such as the urethra FIG. 13, FIG. 14, while the back side 220, may reduce pressure on the colon due to being flush with the cup walls 270. Alternatively, the upper ring 200 may uniformly extend inside the cup walls, or outside the cup walls 270.

Figure 3:
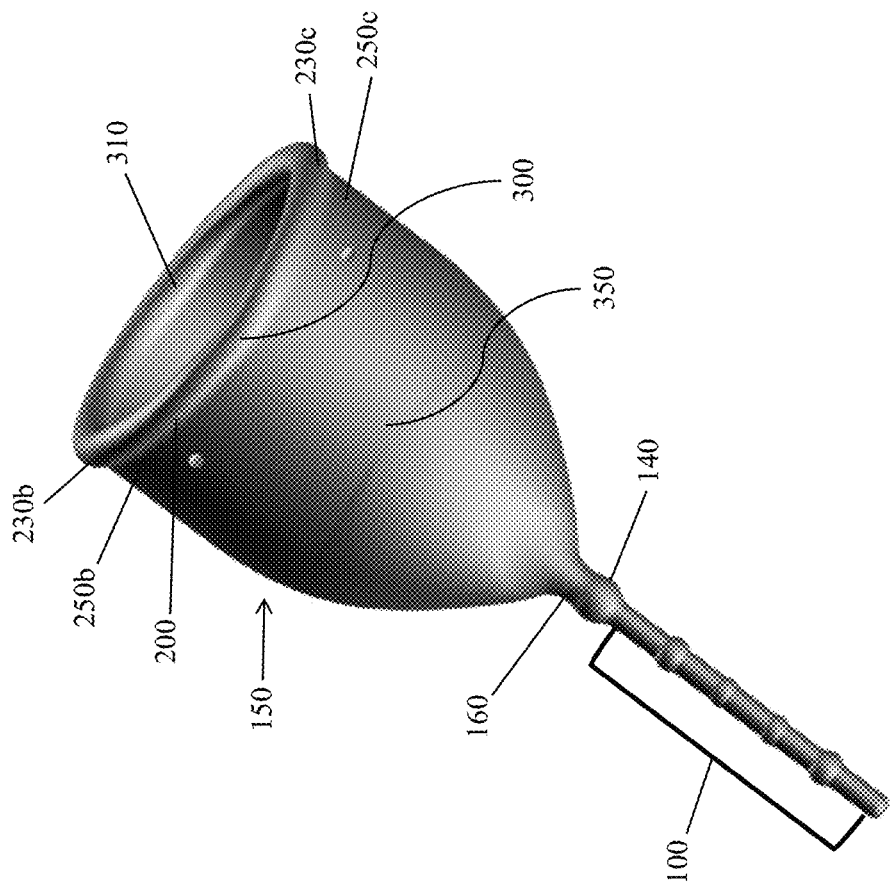
FIG. 3 is perspective view of a menstrual device from the front at an angle of the present invention.

In the exemplary perspective view of FIG. 3, the small removal bulb 140 at the base of the device 160 provides a place to hold securely and pull to remove the device 150. Further comprising, pulling anywhere along the elongated stem 100 or removal bulb 140 downwards, or from side to side can break the seal of the upper ring 200 and ease removal. Further, from this perspective view, the front side of the upper ring 300 is noticeably lower than the back side of the upper ring 310. This is due, in part, to a shorter front wall 350, which is unique in that during removal, the shorter front wall 350 assists in breaking the seal of the upper ring 200, thereby minimizing prolonged suction or discomfort. Further, the shorter front wall 350 provides greater comfort to the user during removal as it allows more flexibility as the now fully opened upper ring 200 is pulled out from the vaginal canal FIG. 14. It should be noted that from this perspective view the sides 230*b*, 230*c* of the upper ring 200 visibly protrude outward from the cup walls 250*b*, 250*c*.

Figure 4:
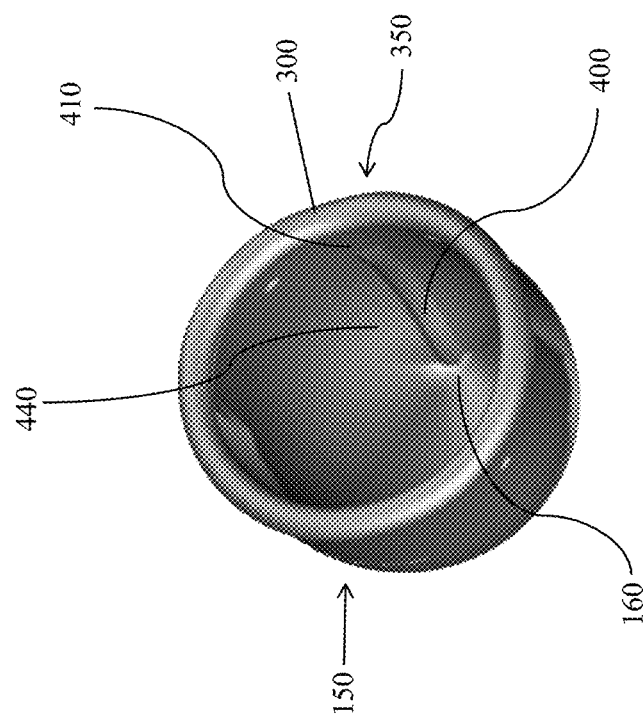
FIG. 4 is a perspective view into the internal walls of a menstrual device at an angle that shows the inside of the front and side walls, as well as the internal spine.

In the exemplary perspective view of FIG. 4, an internal spine 400 extends from the base of the device 160 up the inside wall 440 of the front side of the device 350. Alternatively, the internal spine 400 can, but does not need to, extend the full length of the device 410. This is in part due to the slight dip in the front of the upper ring 300, which assists in creating a crease, fold, or "hinge" when pressure is applied to the front wall 350, as demonstrated in FIG. 8. The internal spine 400 assists in the device 150 folding with pressure applied in one or more locations on the device front wall 350, as demonstrated in FIG. 7 through FIG. 12. Further comprising, the internal spine 400 assists in the device 150 fully opening, once placed inside the vaginal cavity FIG. 14, from the collapsed positioning, as demonstrated in FIG. 10 through FIG. 12. Alternatively, the internal walls 440 of the device 150 remain substantially smooth, without the presence of an internal spine 400 or additional material protruding in width.

Figure 5:
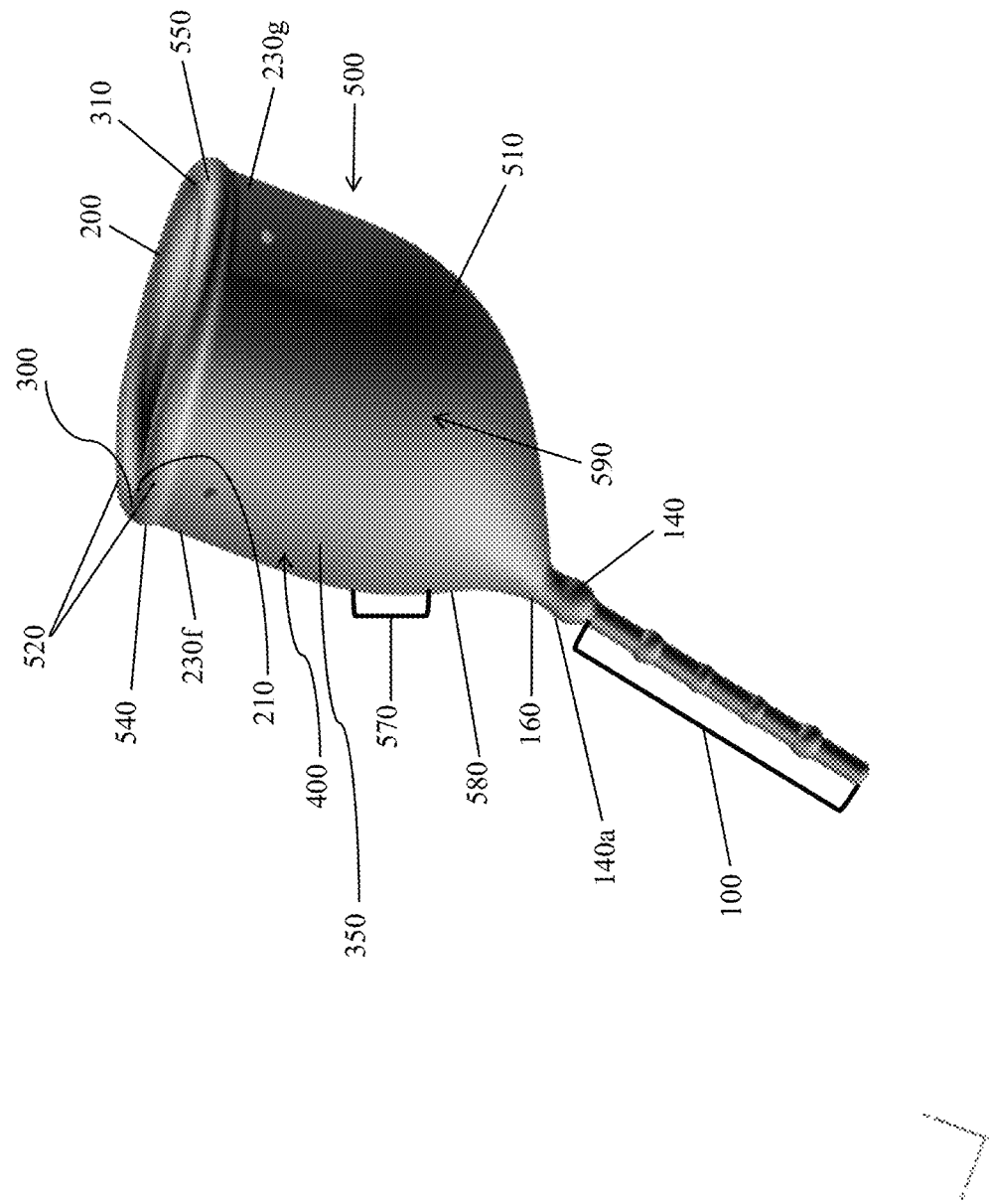
FIG. 5 is a perspective view of a menstrual device from the side.

In the exemplary perspective view of FIG. 5, the front outer edge of the upper ring 540, and back outer edge of the upper ring 550 are flush with the cup walls 230*f*, 230*g*. The front 540 and back 550 upper ring extends between 0.05 mm and 5 mm outwards from the device walls 230*f*, 230*g*. The upper ring 200 has minimal volume of material in order to reduce the amount of pressure in the upper extremities of the device, which is useful because anatomically, the distances between the urethra, vaginal canal, and colon are closer together the further up you go from their openings, so less pressure at the top of the device, 540, 550, 200 is desired to reduce pressure on other organs and bodily functions. The upper ring 200 ranges from 2 mm to 7 mm in width. Further comprising, the specific aspects that are unique in the functioning of the upper ring 200 are that it applies less pressure to critical areas in the front 540 and back 550 of the device to the urethra and colon due to being flush with the device walls 230*f*, 230*g*, thus distributing the pressure instead of intensifying it.

In a second perspective view of FIG. 5, the internal spine 400 and asymmetrical, as demonstrated in FIG. 5, device shape 500 assist the device fully opening once inside the vaginal cavity. This particular design is useful because the upper ring 200, 300, asymmetrical device body 500, internal spine 400, individually, or in concert, helps to create an effective seal. The specific aspects unique in their functioning are that they can eliminate the need for increased skin contact to manually facilitate the device opening fully. Further comprising, this particular design is useful because it can eliminate the uncertainty or guesswork that even the most experienced cup users exhibit as to whether an effective pop open or seal was created.

In a third perspective view of FIG. 5, the asymmetrical shape 500 results in the device opening fully with integrity, and not relying on a stiff upper ring 200 for holding its shape within a constricting space. Further comprising, having a device body 500 with increased integrity and strength due to the asymmetrical shape 500 also eliminates the need for a drastic pop-open, or opening of the of the device upper ring 200, which in this particular design is useful because it reduces the potential for pain, bruising, or soreness in users. Further comprising, it minimizes the intensity of the suction from the seal when removing the device.

Figure 8:
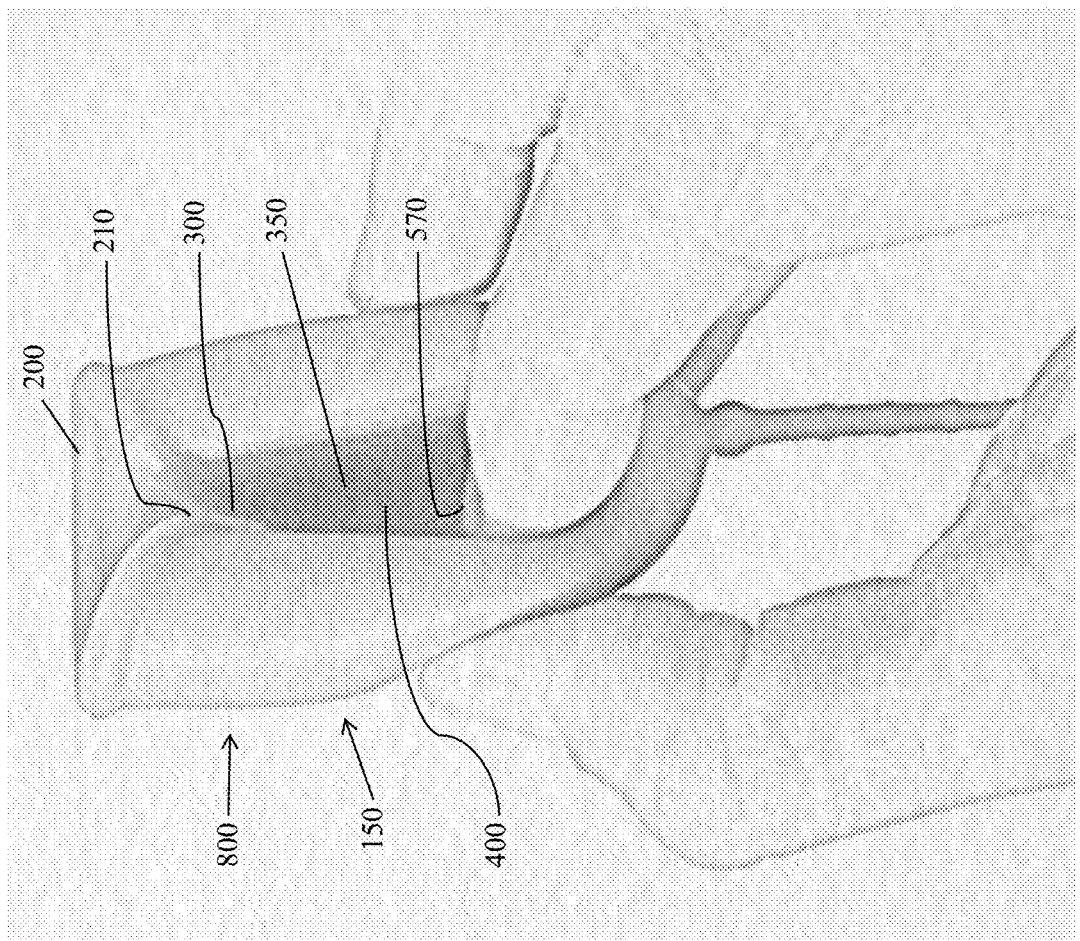
FIG. 8 is a perspective view of a pressure point near the base of a menstrual device being pressed to fold and collapse the device.
Figure 9:
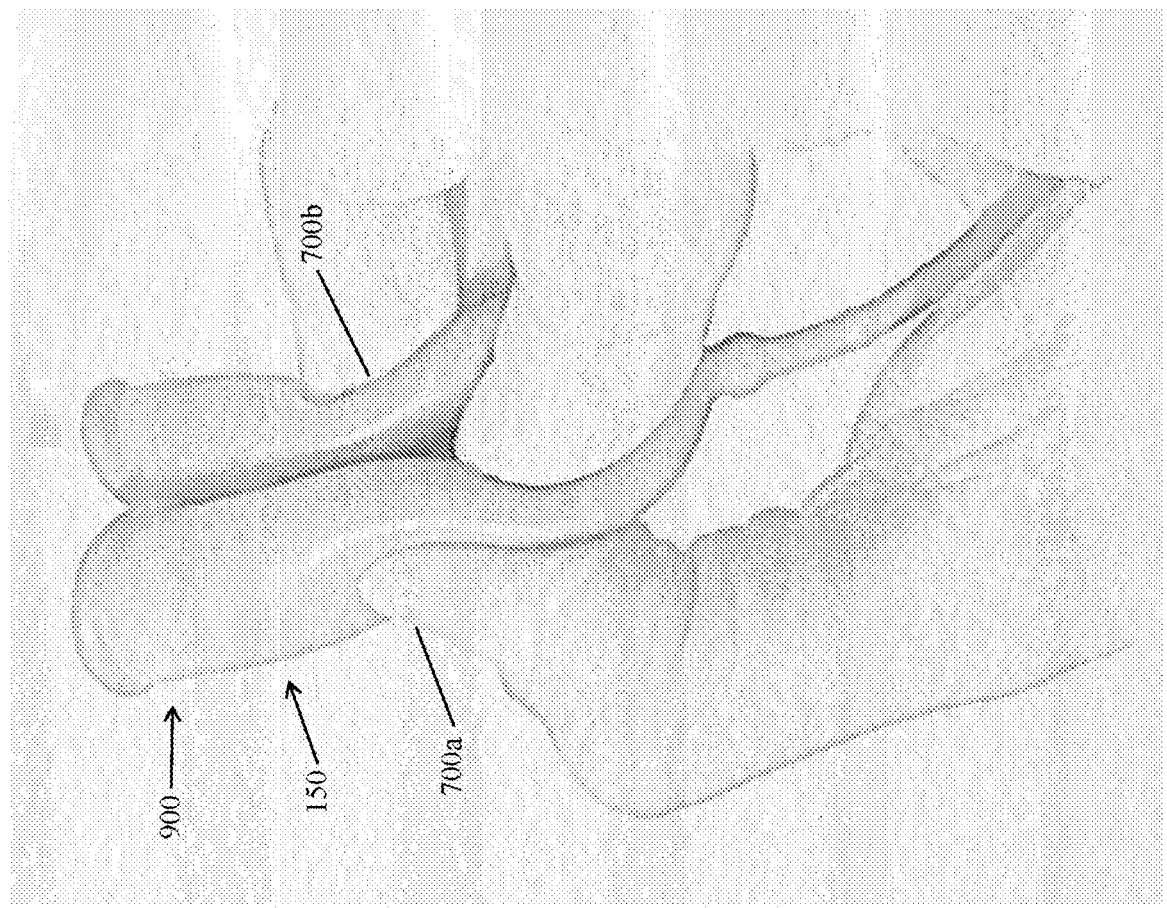
FIG. 9 is a perspective view of a menstrual device folding and side walls being pressed together.
Figure 10:
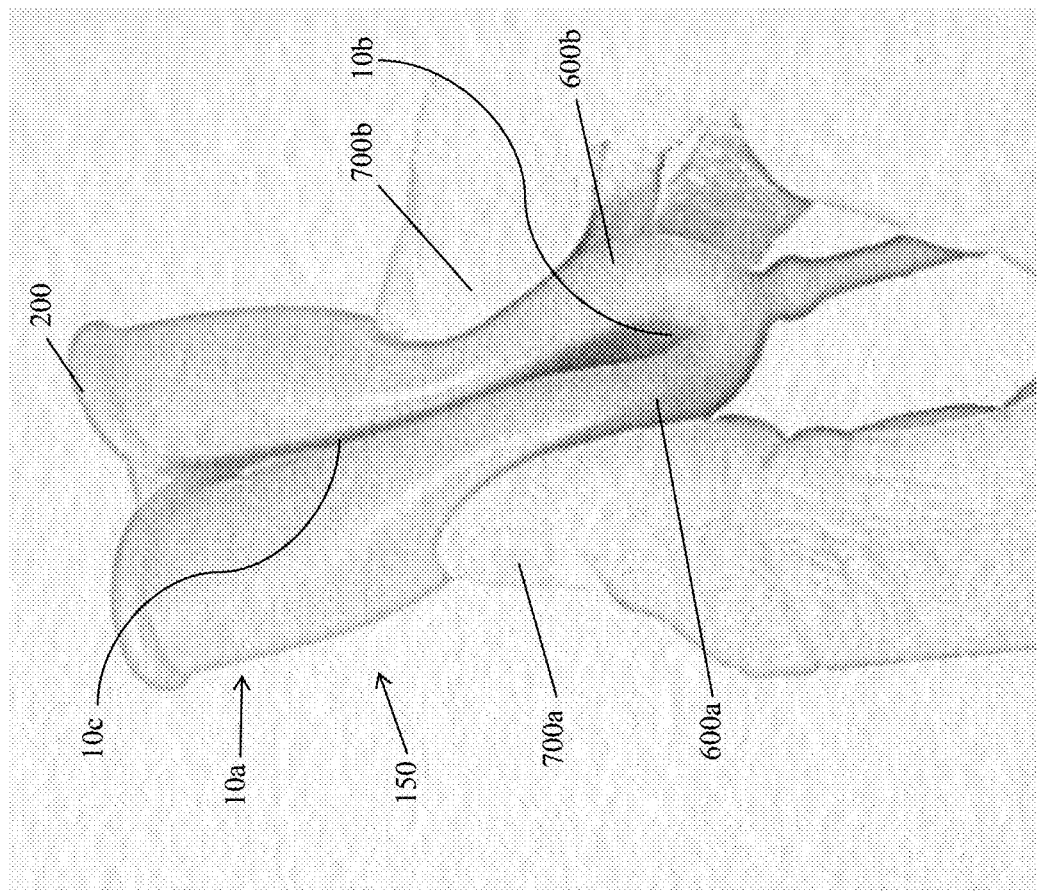
FIG. 10 is a perspective view of a menstrual device collapsed into a fold and held together.
Figure 11:
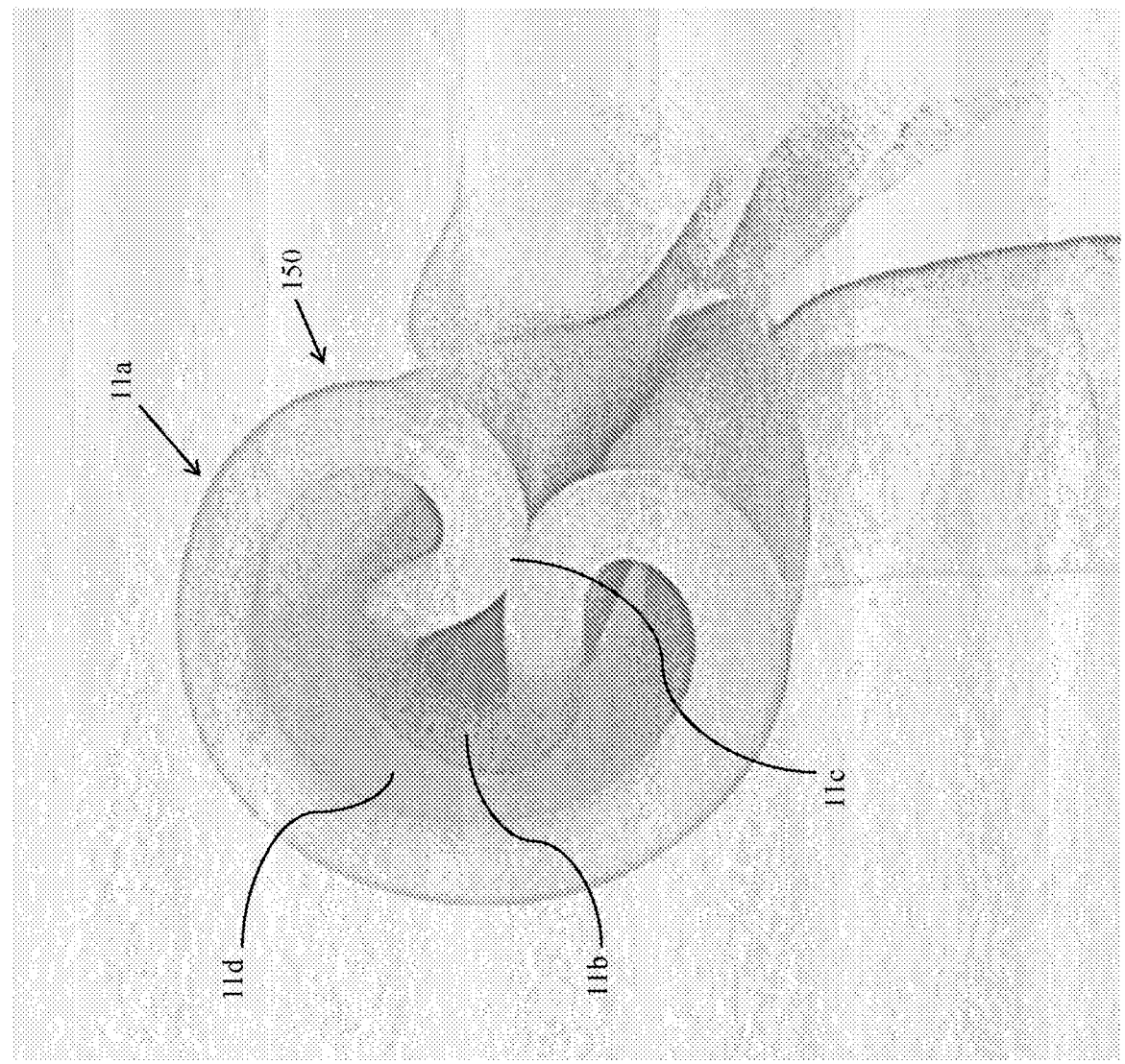
FIG. 11 is a perspective view from the top of a folded menstrual device being held in place.
Figure 12:
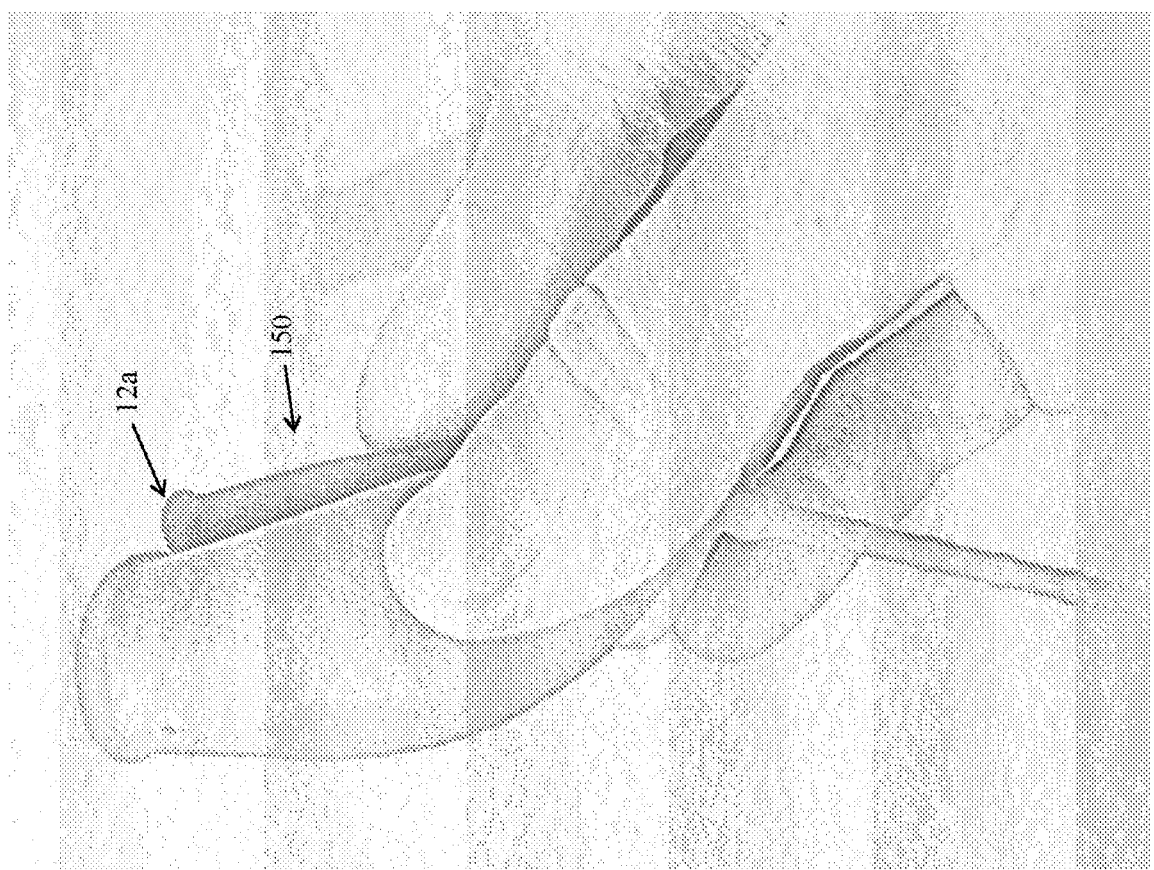
FIG. 12 is a side perspective view of a folded menstrual device ready for insertion into a vaginal canal.

In a fourth perspective view of FIG. 5, a pressure point 570 within the lower third of the device front wall 350 allows for one-handed folding of the device and can eliminate the need for handling and touching upper regions of the device 500 to create a fold, as demonstrated in FIG. 7 through FIG. 12, that collapses the device walls and concentrates the device circumference so as to prepare for insertion into the vaginal canal, FIG. 10 through FIG. 12. Further comprising, the asymmetrical device 500 also curves 580 towards the base 160 from near the pressure point 570. This particular curvature 580 near the pressure point is useful because it helps the user to identify the front side of the cup 350 from near the base 160, the location of the pressure point 570, as well as conforms to contours within the vaginal wall FIG. 13 and FIG. 14. Further comprising, the curvature 580 minimizes potential for bruising or soreness of pressure placed against the pubic bone, but instead, due to complimentary contours, further assists holding the cup in place FIG. 14. It should be noted that the curvature 580 also enables users to identify from just above the base 160 when placing the device where the front facing wall 350 is located due to the slender curve 580 as opposed to the more bulbous curve of the back side 510, which due to its shape and placement within the vaginal cavity, enables significant collection of fluids.

In a fifth perspective view of FIG. 5, the removal bulb 140 in this particular device is placed forward of the cup center line 590, and angled forward as if towards the user's toes when standing, not directly downwards and parallel to the cup center point 590. This unique placement is useful in that it better conforms to anatomy and compliments contours. Further comprising, the angle 160 enables effective stem 100 placement for function, providing logical placement for removal in that the stem 100 goes towards the vaginal opening, which increases comfort as well since the stem material is not probing into the vaginal canal or into the labia. Similar to how a user using a tampon would need to insert it towards their lower back, and not directly up and towards their head, so too with a menstrual cup, hence the particular asymmetrical location for the removal stem 160, bulb 140, and angle of the stem 100. Further comprising, the unique stem placement not only creates a reference as to the cup placement and location, but also enables the cup to stay in place properly, as opposed to traditional cups that sometimes migrate or move out of position, thus causing discomfort or leaking. Further comprising, placement of the stem slightly forward not only simplifies the location for grabbing hold of the stem and base of the cup, but potentially benefits individuals with reduced mobility as well in that placement slightly forward means not having to reach back as far as traditional stems that are positioned and angled directly down.

In a sixth perspective view of FIG. 5, the upper ring 520, forward of the cup center line 590, is sloping towards the front 300, creating an asymmetrical and sloping upper ring 200 resulting in a higher height in the back wall 310 of the device than the front wall 350. Further, the lower front wall 350 and ring 520 of the device results in less material and device circumference when folding the device 500 in preparation to insert, as is visible in FIG. 11, enabling greater ease and comfort for the user when placing the device. Further comprising, this particular design is useful because with the shorter front wall 350 and the asymmetrical upper ring 520, less pressure 570 is required to create the fold and collapse the device, thereby enabling the option of using the device with just one hand, as well as eliminating the need to touch additional areas of the device. Further comprising, the upper ring 540 material shifts further towards the inner wall 210, thereby is further useful in that it creates an easier "hinge" or crease for the fold when pressure is applied 570 as there is less material that might otherwise bunch and create resistance at 540.

In a seventh perspective view of FIG. 5, the unique shape 500 which allows for substantial volume of menstrual fluid collection, retains the integrity of the device shape, yet conforms to natural bodily contours 510, 580, 160. The overall shape of the device body 500 ensures wall integrity and comfort with its asymmetrical shape 500. This particular asymmetrical shape 500, is useful because the front facing wall 350 has the slight curvature 580 that connects to the base 160, while the back wall 510 is more bulbous, with curvature that conforms to the female anatomy. Further comprising, the angle of the upper ring 520 assists users who may have a lower cervix, thereby possibly eliminating: potential disruption of proper placement within the vaginal canal; interference with the device fully opening; or possible bruising of the cervix. Further comprising, the removal bulb 140 has the option to be asymmetrical with less material protruding on the front facing side 140*a* in order to be flush with the vaginal wall, thereby potentially further reducing any pressure.

Figure 6:
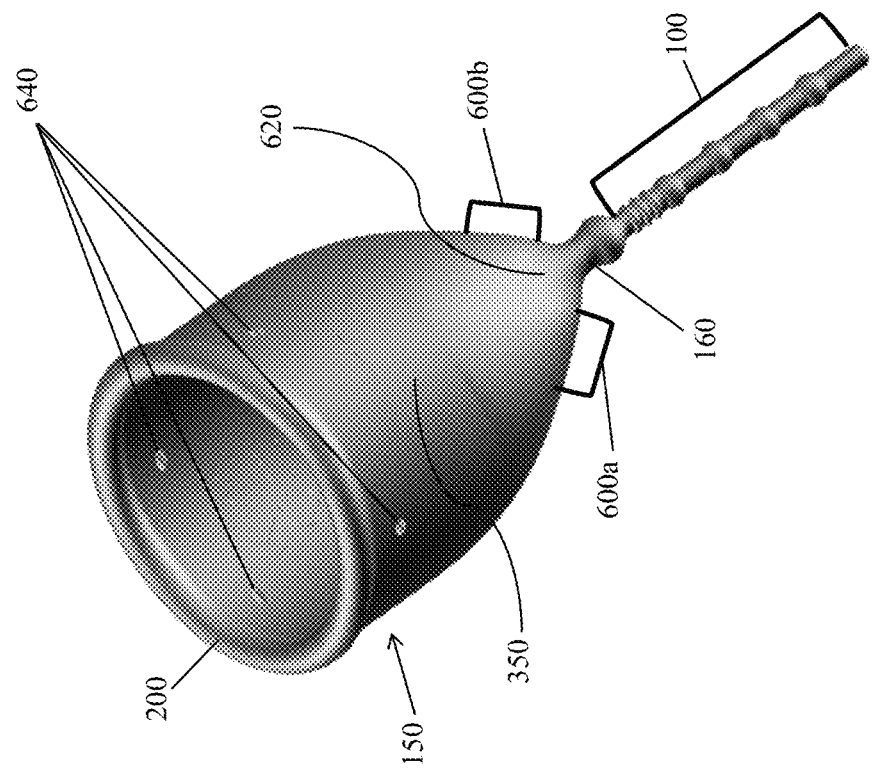
FIG. 6 is a perspective view of a menstrual device from the front at an upper angle.

In the exemplary perspective view of FIG. 6, the two points 600*a*, 600*b* above the device base 160, equidistant from the front of the device 350, can be pressed or pinched together in order to assist the device fully popping open, if needed, to create the seal of the upper ring 200. The existence of these unique pressure points can be useful if the device does not fully open upon initial placement FIG. 14, because, for example, the user has a tighter vaginal cavity. In which case, the pressure points 600*a*, 600*b* located in the lower quarter of the device 150, can have pressure applied from opposite sides to facilitate opening of the device. This specific aspect is unique in the functioning because it encourages the desired opening of the device with minimal guesswork or contact further up the device and into the vaginal canal to check that the seal 200 is fully intact. Further comprising, the user can determine if the device is fully open from base 620, as opposed to having to reach further into the vaginal canal to manually determine this, due to the fold, as demonstrated in FIG. 10, that the user can feel at the front base 620 of the cup 150. Further comprising, the removal stem 160 has the option of being asymmetrical in shape to further enable flexibility of movement.

In a second perspective view of FIG. 6, if assistance is needed to comfortably and effectively break the seal 200 for removal, direct pressure can be placed gently near the base 620 of the device, which will effectively break the seal of the upper ring 200. Further comprising, a user may gently guide the cup 150 towards the vaginal opening by pulling down or side to side on the stem 100, then when the cup 150 is almost completely removed, holding securely at the now visible and accessible base 160 with the option of pressing gently on the pressure point 620 to break the seal. This approach is possible in part due to the elongated stem 100, as well as the pressure point at the base of the cup 620 functioning in concert with the upper ring 200 to reduce the pressure and circumference of the upper ring 200, thereby better controlling and minimizing potential spillage while emptying menstrual material from the cup.

A third perspective view in FIG. 6 illustrates where the one or more pressure or cup seal holes 640 to balance bodily functions while placed inside the vaginal canal are visible near the upper ring 200 of the device. It should be noted that they are not a unique design feature.

Figure 7:
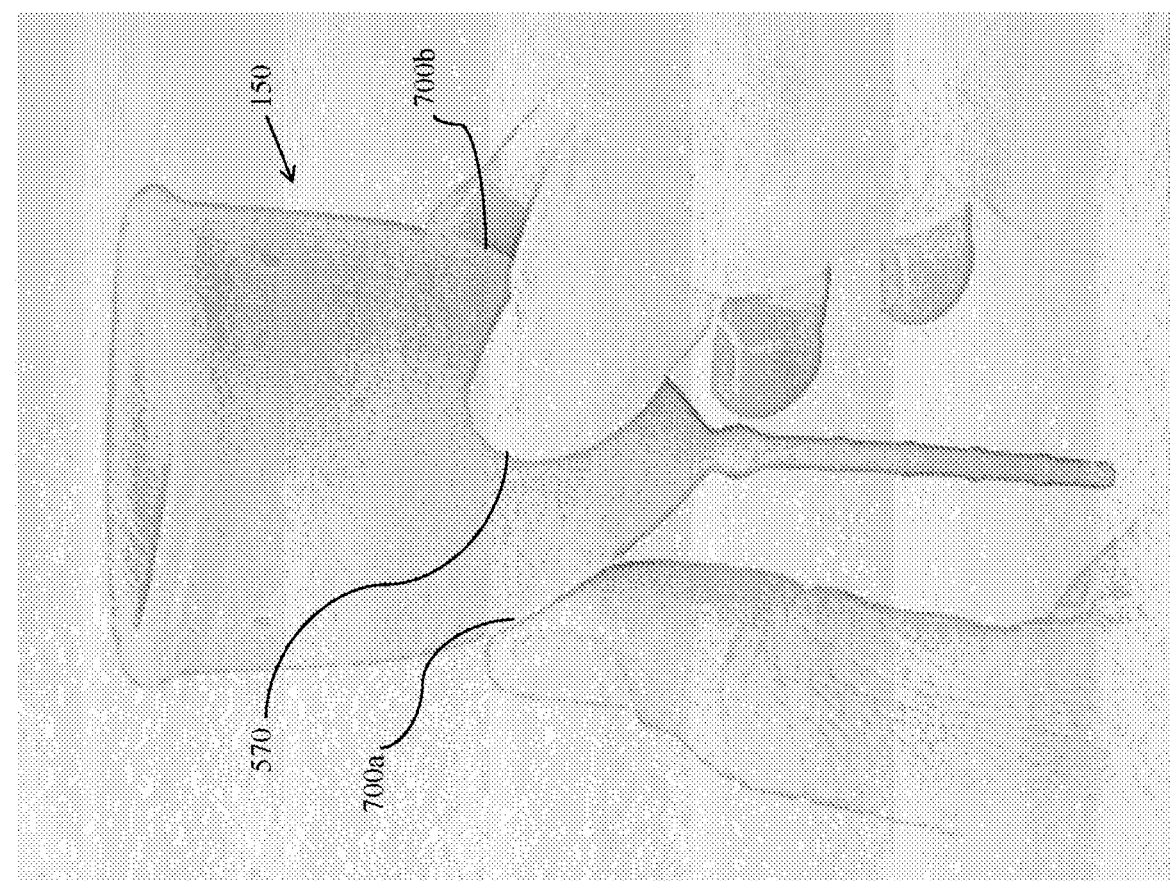
FIG. 7 is a perspective view of holding a menstrual device.

In the exemplary perspective view of FIG. 7, the device 150 is held in one hand with two fingers, such as the thumb and middle finger, on opposite sides of the lower third of the cup body 700*a*, 700*b*, and finger, such as the index finger, touching the pressure point 570. Further comprising, the device 150 has the option of including additional grips or material near the base that extends from the device walls in order to provide additional traction while contacting the cup for collapsing, or for removal.

In the exemplary perspective view of FIG. 8, the device 150 is shown with pressure applied 800 to the front wall 350 at the pressure point 570, which coincides with the internal spine 400. The upper ring 200 is shown collapsing at the front-facing, lowest point 300, further assisted by the upper ring material 210 that extends further into the cup walls, thereby creating a hinge.

In the exemplary perspective view of FIG. 9, the device 150 is shown collapsed 900. Side walls 700*a*, 700*b* continue to be pressed together with the two or more fingers.

In the exemplary perspective view of FIG. 10, the device 150 is shown fully collapsed 10*a*. The fold 10*c* on the front facing side of the cup extends from the upper ring 200 down to the base 10*b*, thereby enabling a user to feel and identify from the base of the cup whether it is fully open or still partially collapsed while it is placed inside the vaginal canal FIG. 14. Further comprising, in the event that the device 150 does not fully open, for example in a user who has a narrower vaginal canal when first inserting the cup, and the pressure collapsing the cup 700*a*, 700*b* is removed, the user may apply pressure on the lower portion of the cup base 600*a*, 600*b*, to encourage full opening of the device.

In the exemplary perspective view of FIG. 11, the device 150 is shown from above in a collapsed configuration 11a. Further comprising, the asymmetrical shape and shorter front wall 11b does not bunch material from the entire upper ring onto each other 11c, but rather is offset 11d in most areas, thus resulting in creating a smaller overall cup dimension when collapsed.

In the exemplary perspective view of FIG. 12, the device 150 is shown fully collapsed 12a and ready for insertion into the vaginal canal.

Figure 13:
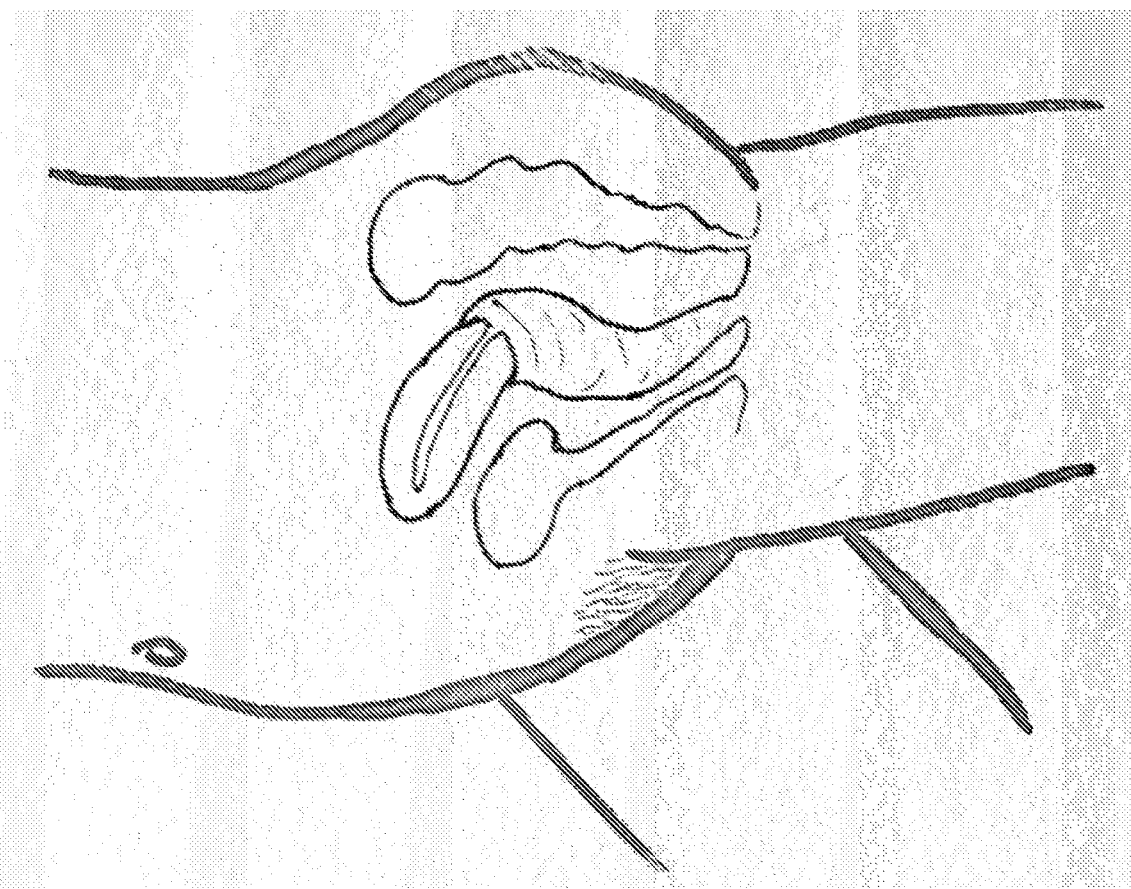
FIG. 13 is a side cutaway view of the female anatomy showing the urethra, vaginal canal, and colon.

In the exemplary perspective view of FIG. 13, an illustration of the female anatomy from a side view is depicted.

Figure 14:
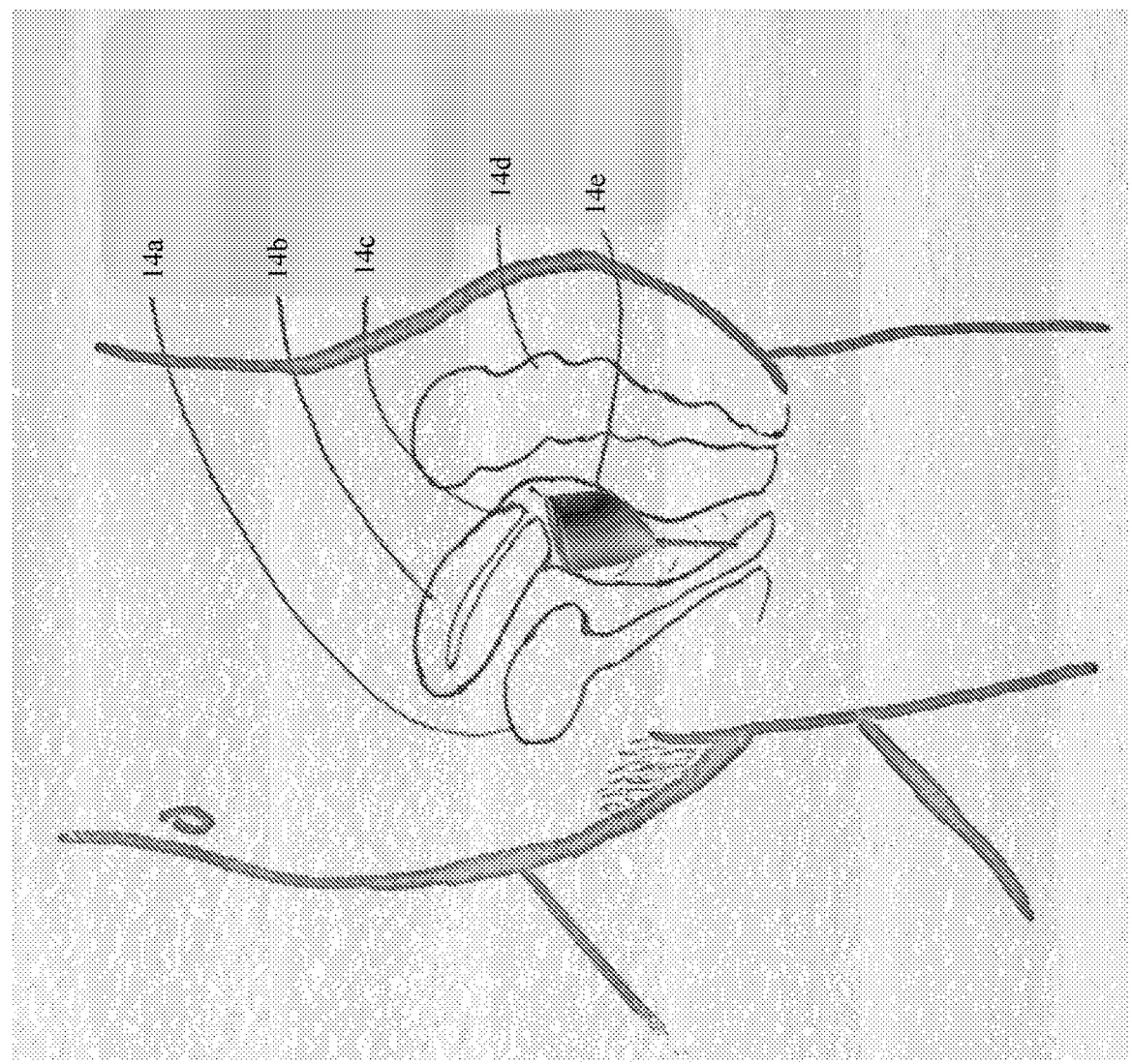
FIG. 14 is a side cutaway view of the female anatomy with a menstrual device placed inside the vaginal canal

In the exemplary perspective view of FIG. 14, an illustration of the female anatomy from a side view is depicted with a menstrual cup placement. Specifically, a menstrual cup is illustrated in FIG. 14 inside a vaginal canal 14e. The female anatomy in FIG. 14 further depicts a bladder 14a with a urethra connected below 14a, a uterus 14b, a cervix 14c and lastly, a colon 14d.

Figure 15:
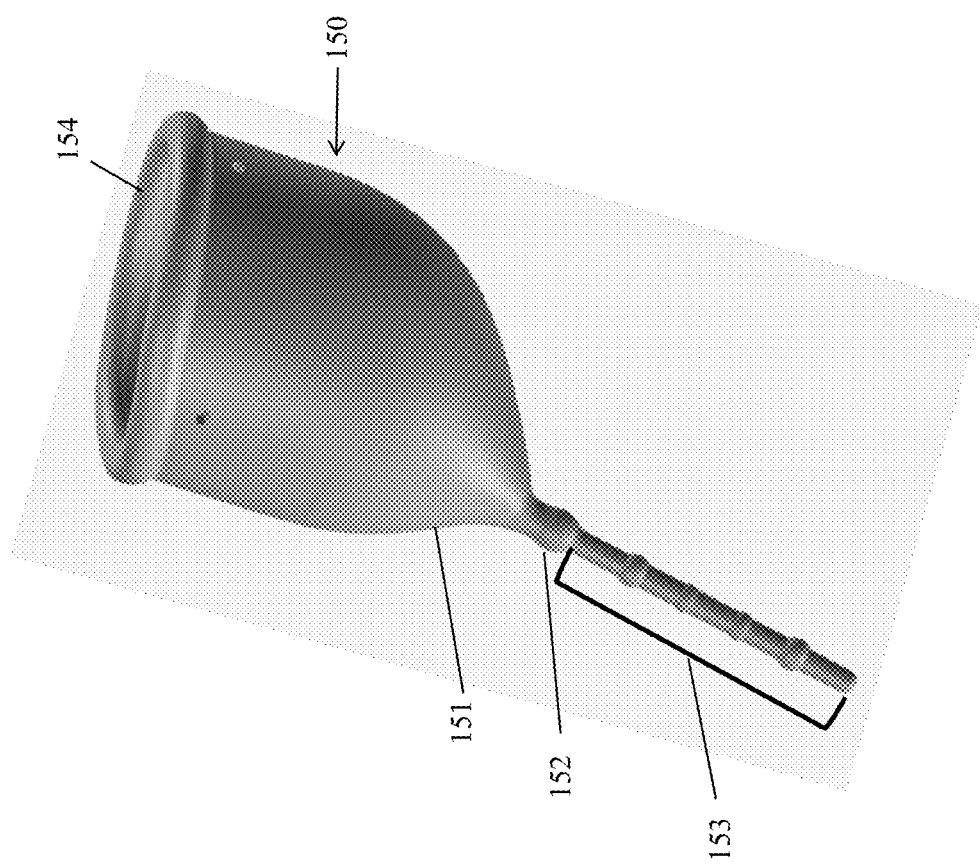
FIG. 15 is a perspective view of an alternate embodiment of a menstrual device from the side.

In the exemplary perspective view of FIG. 15, the device 150 is shown from the side with an alternative curvature at a front base 151 to compliment placement and curvature of the pubic bone. A removal bulb 152 is also depicted, with minimized curvature or extension on the front facing side. A removal stem 153 comprises modified bulb dimensions for gripping and identification on the removal stem 153. An upper ring 154 is also illustrated in FIG. 15 with increased width dimensions so as to further assist in the cup fully opening and creating an effective seal with minimal effort and maneuvering, yet still maintaining optimal flexibility.

Figure 16:
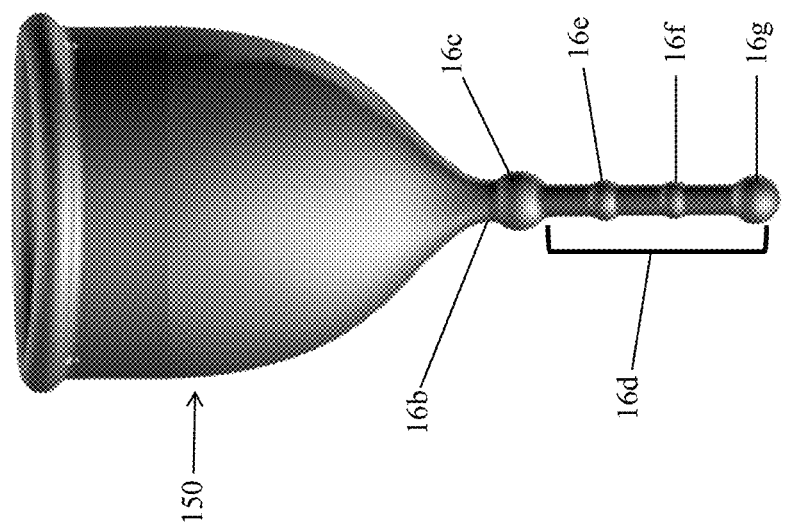
FIG. 16 is a perspective view of an alternate embodiment of a menstrual device from the front with an elongated removal stem in accordance with aspects of the present invention.

In the exemplary perspective view of FIG. 16, the device 150 is shown in a smaller size in comparison to the previous devices depicted with smaller overall length and dimensions and alternative design from the front. As shown in FIG. 16, a transition from a cup base to a stem 16b is elongated to allow room for gripping and accommodate the spacing of the pubic bone. The width of a removal bulb 16c extends further on the sides to enable better gripping from the sides and minimize slipping while still keeping the overall flexibility and minimized profile and extension front to back. An elongated removal stem 16d is of varying width with varying dimensions in bulbs 16e, and 16f, and finally at the tip of the removal stem 16d with a larger bulb 16g for gripping when removing by pulling slightly down and side to side to both break the seal safely, and lower the cup down such that the cup base 16b is in reach. The removal stem 16d enables flexibility, yet strength so that it does not stretch extensively and minimizes potential for a snapping back if the grip slips.

Figure 17:
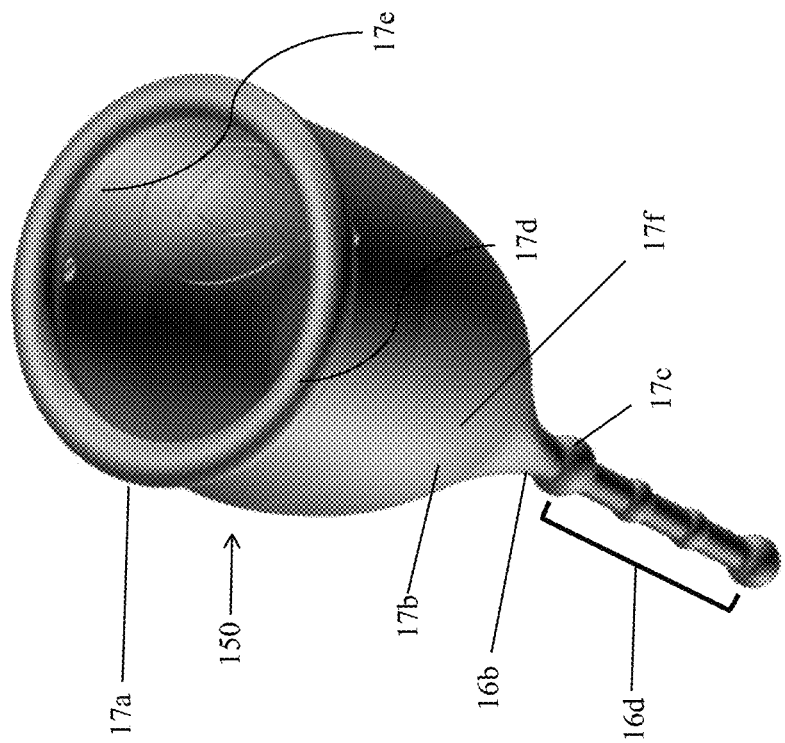
FIG. 17 is perspective view of an alternate embodiment menstrual device from the front at a slightly elevated angle of the present invention.

In the exemplary perspective view of FIG. 17, the device 150 is shown from the front at an upper, slightly side view angle. An upper ring 17a is of smaller diameter as compared to the diameter of the upper ring 200 of a similar design and has the option of a uniform width. Alternatively, the upper ring 17a can have varying dimensions with varying extensions both outward and inward from the cup walls. The cup dimensions may begin to taper, especially on a front wall 17b towards a cup base 16b. Point 17f also serves as the location of the pressure point for collapse as well as for helping break the seal of the upper ring 17a. Further, from this perspective, an alternative view of the removal bulb 17c and the asymmetrical shape and angles is depicted. Further comprising, 17d is where the front wall of cup hinges for the collapse during insertion. Alternatively, other embodiments might have variations of width and extensions outward or inward from the cup walls 150. The inner angle of the upper ring 17e extends flush in the transition with the cup walls so that this embodiment with slightly more material on the inner facing sections of the upper ring 17a might provide increased firmness and rigidity for ease of creating a seal and having the cup fully open with the upper ring 17a making full contact all the way around against the vaginal wall. This embodiment of the inner angle of the upper ring 17e further allows increased rigidity without excessive material protruding on the outer diameter 17a.

Figure 18:
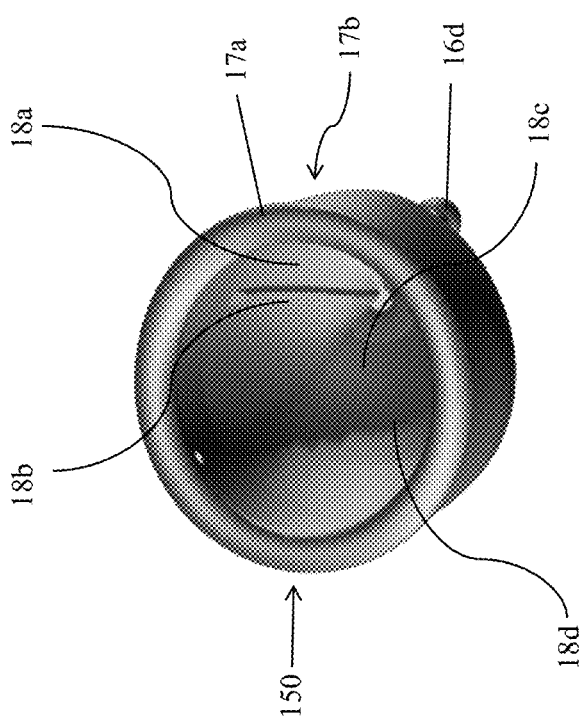
FIG. 18 is a perspective view into the internal walls of an alternate embodiment menstrual device at an angle that shows the inside of the front and side walls, as well as the internal spine.

In the exemplary perspective view of FIG. 18, the device 150 is shown from the front at an upper angle, from the back side so as to see the inside of a cup 18c and inside of a front wall 18a. Further comprising, from this angle an internal spine 18b is shown, which assists in the collapsing of the cup with a pressure point 17b, as well as in the cup upper ring 17a fully opening once the collapsed cup (FIG. 10) is released. Additionally, the internal spine 18b provides overall integrity and strength to an otherwise uniform wall 18a thickness and serves as structural reinforcement during collapsing, opening, as well as the material connecting to the removal stem 16d. A more bulbous back curvature 18d of the cup enables larger capacity for collection while complimenting the anatomical, ergonomic needs.

Figure 19:
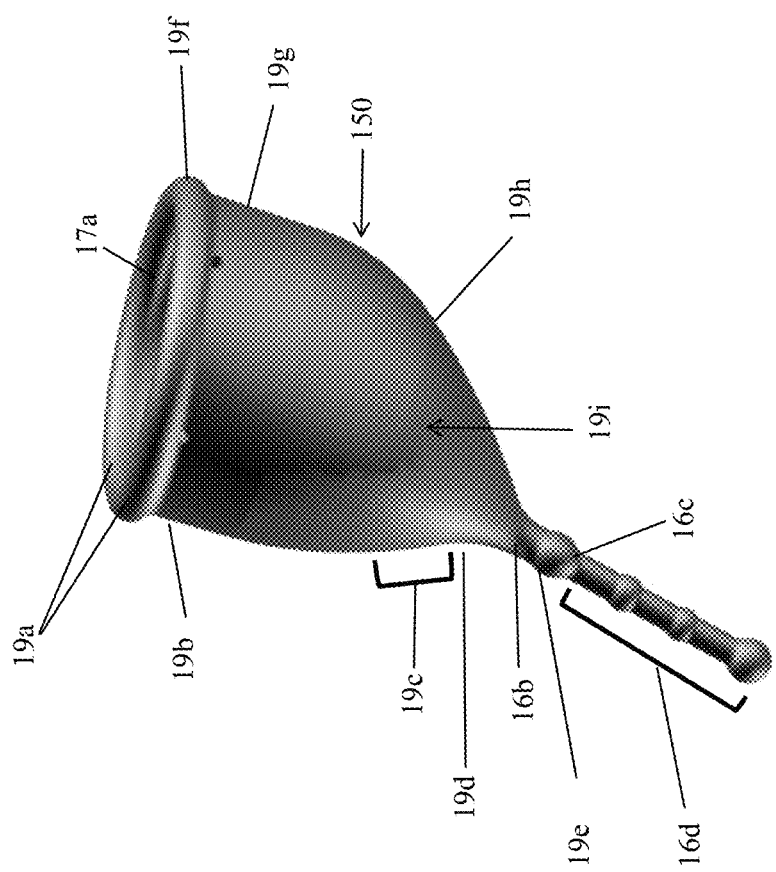
FIG. 19 is a perspective view of an alternate embodiment menstrual device of an alternate design, dimensions, and features such as the overall device shape of ergonomic curvature, and removal stem from the side.

In the exemplary perspective view of FIG. 19, the device 150 is shown from the front at a side view. The device 150 includes an upper ring 17a, forward of a center point 19i of the cup of the device 150, which angles downward at a slant 19a so as to enable a cleaner removal in part due to a wall height 19b. Additionally, the angle 19a allows for the seal to break organically at an earlier point during removal and is less dependent on the user properly following safe removal practices to minimize stress or suction to their body. The overall wall height 19b is lower on the front of the cup, compared to a back wall 19g and an upper ring 19f of the device 150, which further helps with regards to potential cervix interference in those with lower cervixes, as well as minimizing overall circumference of the upper ring 17a during removal to allow greater comfort and ease. The angle of the front lower wall 19d of the device 150 is such that it conforms to the pubic bone. Therefore, a pressure point 19c used during collapse is accomplished with greater ease due to spacing and angle for the index finger to apply pressure (see FIG. 8). Additionally, during removal, the pressure point 19c to assist in breaking the seal may begin to be pressed upon by the pubic bone when the user pulls down and side to side on the removal stem 16d or the removal bulb 16c at the cup base 16b. Further comprising, the front of the removal bulb 19e is almost flush so that it does not create any specific points of rubbing if the cup ends up settling or positioning itself against the pubic bone or entry of the vaginal canal while sitting, for example. A side view of the cup base center point 19i demonstrates the tapering of the device 150 from the more bulbous angle 19h that enables users with a comfortable glide during insertion and removal, and overall ergonomic fit once placed and fully opened. A bulbous curvature 19h enables greater capacity for menstrual fluid collection, while optimizing overall vaginal morphology for optimal fit without the need for a cup shape or size that feels noticeable, bulky, or causes undue pressure. The angle of the removal stem 16d and tapered cup base of device 150 allows for natural placement easily reached by its forward position while also minimizing the poking or rubbing against the body that can often occur with stems that are placed in the geometric center of the cup. This stem angle 16d and device 150 angle forward of the center point 19i allows the cup to be comfortable in numerous positions, including sitting.

Figure 20:
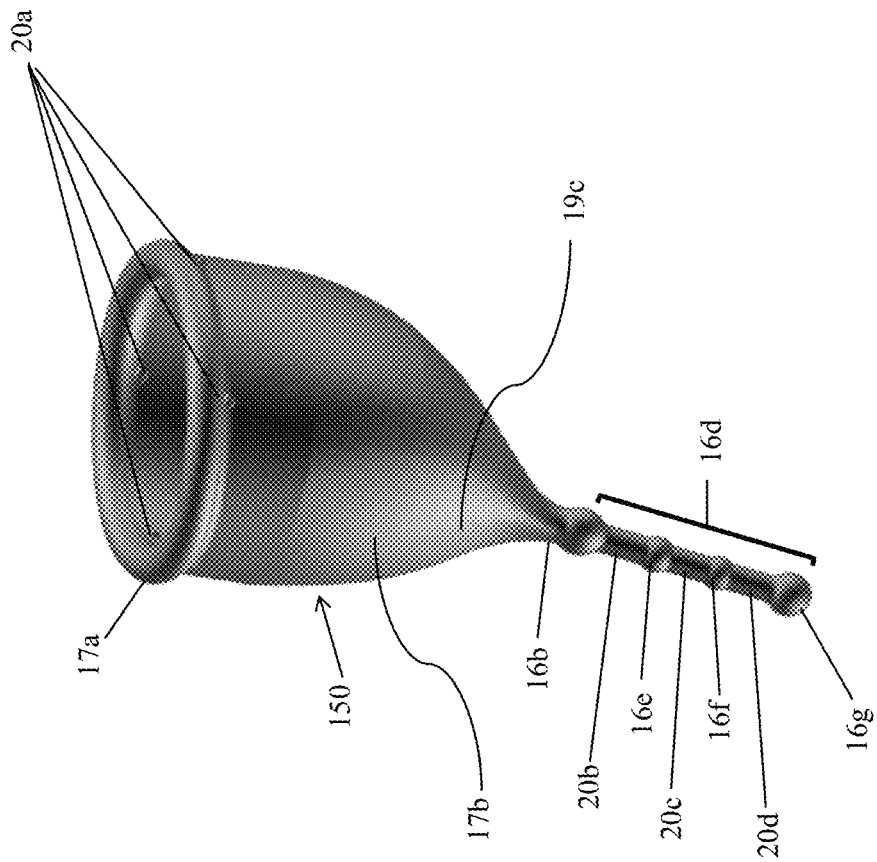
FIG. 20 is a perspective view of an alternate embodiment menstrual device with varying stem width and grip, and device body from the front at an upper angle.

In the exemplary perspective view of FIG. 20, the device 150 is shown from the front at an upper, slightly side view angle. Varying stem width 20b, 20c, 20d, and grip width of the bulbs on the stem 16e, 16f, 16g, enable flexibility, comfort, and functionality in an intuitive removal stem. A removal bulb at the base 16g has enough material to grasp so as to further allow ease of removal, while having the option to do so with minimized contact of the upper areas of the cup 150 until the cup base 16b is within reach, at which point, the pressure point 19c can be used to break the seal if still needed. The gentle tapering of the cup body 150 creates a more subtle transition and experience during removal. Upper holes 20a, though not a unique design feature, assist in breaking the seal and maintain an equilibrium during use, and are placed quite near the upper ring 17a so as to allow maximum capacity during use.

Figure 21:
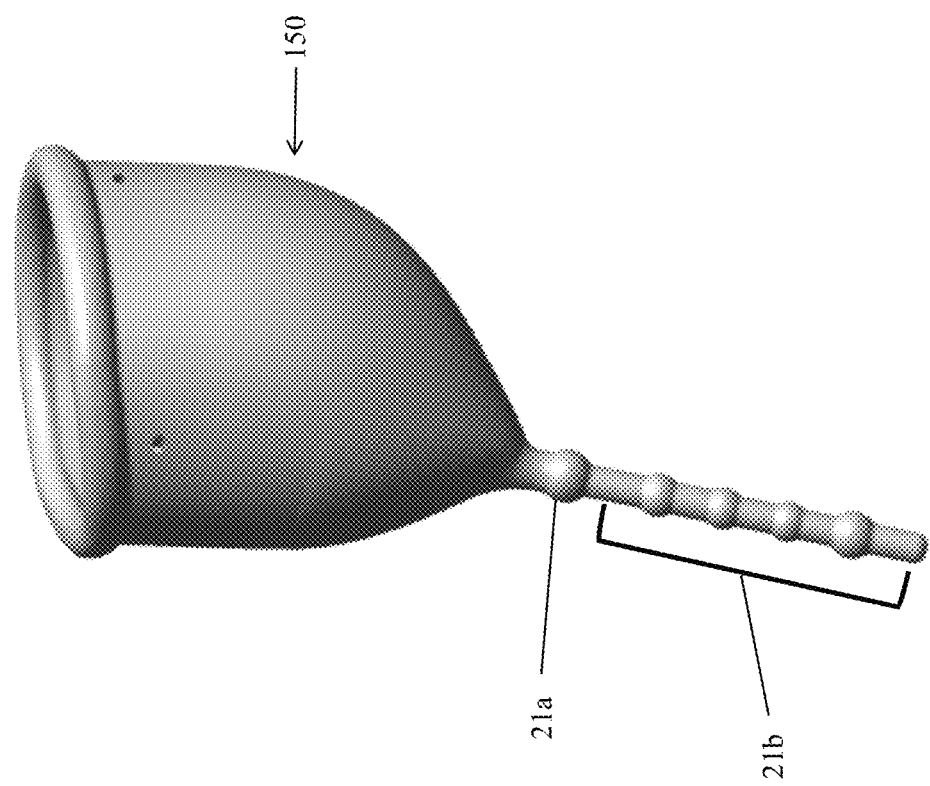
FIG. 21 is a perspective view of an alternate embodiment menstrual device of an alternate design, dimensions, and features such as the removal bulb, stem, and removal grips on the stem from a side angle.

In the exemplary perspective view of FIG. 21, the device 150 is shown from the side with a profile view of an asymmetrical removal bulb 21a depicted, with minimized curvature or extension on the front facing side. A removal stem 21b comprises modified and varying stem widths and bulb dimensions for gripping and identification on the removal stem 21b while providing flexibility in movement, strength as well as sufficient material for gripping.

Figure 22:
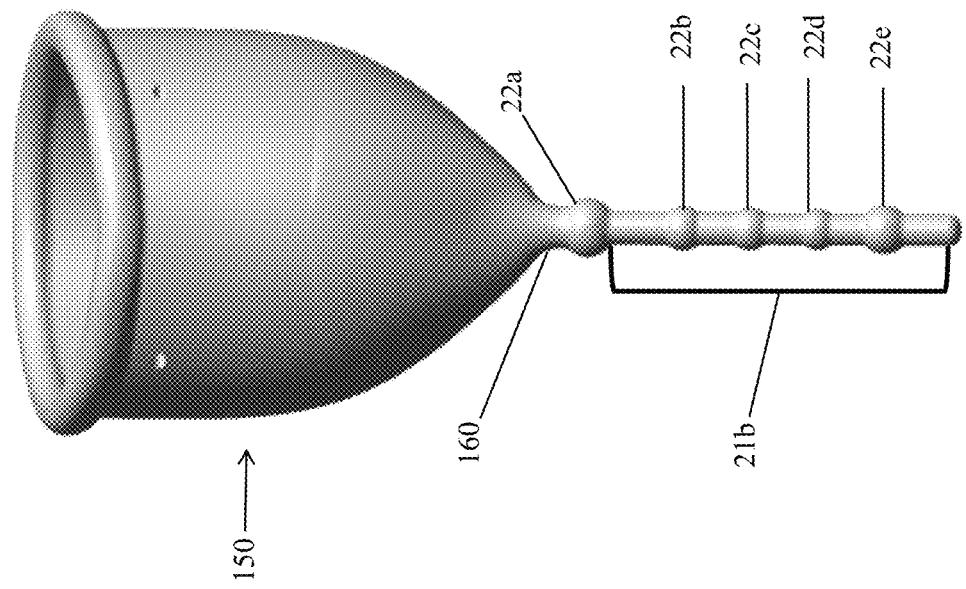
FIG. 22 is a perspective view of an alternate embodiment of a menstrual device from the front with an asymmetrical elongated removal stem, removal bulb, and varying stem and grip dimensions in accordance with aspects of the present invention.

In the exemplary perspective view of FIG. 22, the device 150 is shown from the front with the extending width of an asymmetrical removal bulb 21b depicted. A removal stem 21b comprises modified and varying stem widths between each bulb, 22a, 22b, 22c, 22d, 22e with varying dimensions. The stem 21b, while narrowing in width from the cup base 160 to the tip of the removal stem 21b allows both strength and flexibility for comfort and function. The final removal bulb at the tip 22e, enables more substantial gripping capabilities than the bulbs in the middle section 22b, 22c, and 22d.

These, along with other details of this unique design, will become more apparent in the following claims and drawings. It is understood that there may be some changes to the exact structure described and shown, but they do not negate the overall spirit of the invention. Further, features described in the preceding description may be used in combinations other than the combinations explicitly described.

Whilst aiming to draw attention to features of the invention believed to be of particular importance, it should be understood that the Applicant claims protection in respect of any patentable feature or combination of features hereinbefore referred to and/or shown in the drawings whether or not particular emphasis has been placed thereon.

The term "comprising" as used in the claims does not exclude other elements or steps. The term "a" or "an" as used in the claims does not exclude a plurality. A unit or other means may fulfill the functions of several units or means recited in the claims.

What is claimed is:

1. A device for collecting and holding menstrual fluids within a user's body, the device comprising:
    an asymmetrical cup that tapers downward to a base, wherein the asymmetrical cup is open at an upper edge to collect the menstrual fluid, and closed at a lower edge to contain the fluid in the cup, the cup further comprising:
        an inner wall configured to contact the collected menstrual fluid;
        an outer wall configured to contact and form a seal against a user's vaginal wall; and
    at least one pressure point on the asymmetrical cup;
    an upper ring that extends outwards from the upper edge of the cup, wherein the upper ring is substantially flush with the outer wall on an upper, front facing side of the cup, the upper ring extending inside the cup walls, thereby minimizing pressure on a urethra of the user; and
    an asymmetrical, elongated removal stem singly molded with the base of the device in uniform material, extending downward from the base of the cup, the stem configured to be adapted to extend an elongated length from the base of the cup.

2. The device of claim 1, wherein the asymmetrical, elongated removal stem comprises at least one of varying dimensions and grips.

3. The device of claim 1, wherein the elongated removal stem is configured for securing the asymmetrical cup in place.

4. The device of claim 3, wherein the elongated removal stem includes an elongated length configured to assist the user for easy retrieval and removal of the device from the user's body.

5. The device of claim 1, further comprising a removal bulb having an asymmetrical shape.

6. The device of claim 3, further comprising a bulb at a base or end of the elongated removal stem, the bulb configured to couple to a connector configured to assist in removal of the device from the user's vaginal cavity.

7. The device of claim 1, wherein an angle of the base of the cup tapers such that the device is form-fitting to the user's vaginal anatomy.

8. The device of claim 1, wherein the upper ring is angled and located on a front wall of the asymmetrical device, the upper ring configured in such way as to assist in breaking the seal during removal of the device from the user's vaginal cavity.

9. The device of claim 1, wherein the elongated removal stem and the base of the asymmetrical cup are both positioned at an angle forward of a center line of the cup.

10. The device of claim 1, wherein the asymmetrical cup further comprises an upper ring having less firmness as compared to the rest of the asymmetrical cup.

11. A method for removing a device by a user from a user's vaginal cavity, the device having a cup body, the method comprising:
    moving an elongated and asymmetrical removal stem coupled to the cup body of the device in a side to side motion; and
    pulling down the elongated and asymmetrical removal stem, thereby breaking the suction seal of the device from the user's vaginal cavity in such a way as to minimize the user's contact with the cup body.

12. A method for collapsing a device for insertion by a user into a vaginal cavity, the device having an asymmetrical cup and an asymmetrical base, and an upper ring of the asymmetrical cup also being asymmetrical, the method comprising:
    placing pressure using a finger on at least two locations of an outer wall of the device;
    pressing a center pressure point on a shorter wall of the asymmetrical cup;
    pressing and collapsing the outer wall together;
    removing the finger from the center pressure point and holding device material together;
    inserting the device into the vaginal cavity; and
    removing the pressure, thereby allowing the device to open.

13. The method of claim 12, wherein the steps of placing pressure using the finger on at least two locations of the outer wall of the device, pressing the center pressure point on the shorter wall of asymmetrical cup, and pressing and collapsing the outer wall together are accomplished by using one hand.

14. The method of claim 12, further comprising the step of fully opening the device to create a seal of the upper ring by pressing at least one pressure point area near the asymmetrical base of the device.

15. The method of claim 14, further comprising the step of breaking the seal for removal from or near the base of the device by pulling an elongated removal stem of the device.

16. The method of claim 14, further comprising the step of breaking the seal for removal from or near the asymmetrical base of the device due to an angled upper ring of the cup.

17. The method of claim 14, further comprising the step of breaking the seal for removal from or near the asymmetrical base of the device by pulling a removal bulb of the device.

18. The method of claim 12, further comprising the step of applying pressure near the asymmetrical base of the device.

19. The method of claim 12, wherein the upper ring of the asymmetrical cup is configured to allow the asymmetrical cup to collapse in a more compact manner, thereby resulting in a small insertion point of entry for cup insertion.

* * * * *